United States Patent [19]
Araneo et al.

[11] Patent Number: 6,150,348
[45] Date of Patent: Nov. 21, 2000

[54] METHODS FOR PREVENTING PROGRESSIVE TISSUE NECROSIS, REPERFUSION INJURY, BACTERIAL TRANSLOCATION AND ADULT RESPIRATORY DISTRESS SYNDROME

[75] Inventors: Barbara A. Araneo, Salt Lake City; Raymond A. Daynes, Park City, both of Utah; Urszula Orlinska, Hockessin, Del.; Imad S. Farrukh, Salt Lake City, Utah

[73] Assignees: University of Utah Research Foundation; Pharmadigm, Inc., both of Salt Lake City, Utah

[21] Appl. No.: 09/311,282

[22] Filed: May 14, 1999

Related U.S. Application Data

[60] Division of application No. 08/870,234, Jun. 5, 1997, Pat. No. 5,977,095, which is a continuation-in-part of application No. 08/580,716, Dec. 29, 1995, Pat. No. 5,753,640, and a continuation-in-part of application No. 08/516,540, Aug. 18, 1995, Pat. No. 5,846,963, said application No. 08/580,716, is a continuation-in-part of application No. 08/516,540, said application No. 08/516,540, is a continuation-in-part of application No. 08/480,744, Jun. 7, 1995, Pat. No. 5,587,369, which is a continuation-in-part of application No. 08/480,745, Jun. 7, 1995, Pat. No. 5,635,496, which is a continuation-in-part of application No. 08/480,747, Jun. 7, 1995, Pat. No. 5,811,418, and a continuation-in-part of application No. 08/480,748, Jun. 7, 1995, Pat. No. 5,686,438, said application No. 08/480,744, is a continuation-in-part of application No. 08/284,688, Aug. 9, 1994, Pat. No. 5,532,230, which is a continuation-in-part of application No. 08/029,442, Mar. 11, 1993, abandoned.

[51] Int. Cl.$^7$ .................................................... A61K 31/56
[52] U.S. Cl. ........................ 514/178; 514/169; 514/177; 514/182
[58] Field of Search ...................... 514/169, 177, 514/178, 182

[56] References Cited

U.S. PATENT DOCUMENTS

| | | |
|---|---|---|
| 4,898,694 | 2/1990 | Schwartz et al. |
| 5,001,119 | 3/1991 | Schwartz et al. |
| 5,110,810 | 5/1992 | Eich et al. |
| 5,162,198 | 11/1992 | Eich et al. |
| 5,175,154 | 12/1992 | Schwartz et al. |
| 5,206,008 | 4/1993 | Loria . |
| 5,489,581 | 2/1996 | Daynes et al. |
| 5,532,230 | 7/1996 | Daynes et al. |
| 5,587,369 | 12/1996 | Daynes et al. |
| 5,635,496 | 6/1997 | Daynes et al. |
| 5,686,438 | 11/1997 | Daynes et al. |

OTHER PUBLICATIONS

R.H. Simon et al. (1992). "Adult Respiratory Distress Syndrome," *Inflammation: Basic Principles and Clinical Correlates*, J.I. Gallin et al., eds., Raven Press, NY, pp. 999–1016.

A. W. Meikle et al. (1991). "Adrenal Androgen Secretion and Biologic Effects," *Endocrin. & Metab. Clinics of North America*, vol. 20, No. 2, pp. 381–400.

N.B. Vedder et al. (1990). "Inhibition of leukocyte adherence . . . in rabbit ear," *Proc. Natl. Acad. Sci. USA*, vol. 87, pp. 2643–2646.

R. Dolocek (1989). "Endocrine Changes after Burn Trauma—A Review," *Keio J. Med.* 38(3), pp. 262–276.

G Gordon et al., "Modulation of Growth, Differentiation and Carcinogensis by Dehydroepiandrosterone," *Adv. Enz. Regul.* 26:355–365 and 367–378, 1987.

H.P. Ehrlich (1984). "Anti–inflammatory Drugs in the Vascular Response to Burn Injury," *J. Trauma*, vol. 24(4), pp. 311–317.

M.C. Robson et al. (1979). "The Effect of Prostaglandins . . . by Specific Pharmacological Agents," *Plastic & Reconst. Surgery*, vol. 63(6), pp. 781–787.

J.E. Heffner et al. (1989). "Human Platelets Modulate Edema Formation in Isolated Rabbit Lungs," *J. Clin. Invest.*, vol. 84, pp. 757–764.

D. Ben–Nathan et al. (1992). "Protective Effect of Dehydroepiandrosterone (DHEA) in Viral and Bacterial Infections," Abstract from *Public Health Reviews* 1992/93:20, Israel Soc. for Microbiol., p. 177.

W. Yotis et al. (1968). "Antimicrobial properties of testosterone and its intermediates," *Antonie van Leeuwenhoek* 34:275–286.

M.C. Robson et al. (1980). "Increasing Dermal Perfusion after Burning by Decreasing Thromboxane Production," *J. Trauma*, vol. 20(9), pp. 722–725.

G.B. Gordon et al. (1988). "Reduction of Atherosclerosis by Administration of Dehydroepiandrosterone," *J. Clin. Invest.*, vol. 82, pp. 712–720.

D.M. Eich et al. (1993). "Inhibition of Accelerated Coronary Atherosclerosis with Dehydropiandrosterone . . . of Cardiac Transplantation," *Circulation*, vol. 87(1), pp. 261–269.

B.A. Araneo et al. (1993). "Administration of Dehydroepiandrosterone to Burned Mice Preserves Normal Immunologic Competence," *Arch. Surg.* vol. 128, pp. 318–324.

R.M. Loria et al. (1990). "Immune Response Facilitation and Resistance to Virus . . . (DHEA)," *The Biologic Role of Dehydroepiandrosterone*, M. Kalimi et al., eds., W. de Gruyter, Berlin, pp. 107–130.

*Primary Examiner*—Barbara Badio
*Attorney, Agent, or Firm*—Rothwell, Figg, Ernst & Manbeck, p.c.

[57] ABSTRACT

The present invention is related to a method for preventing or reducing the effects of ischemia. The ischemia may be associated with injury or reperfusion injury, such as occurs as a result of infarctions, thermal injury (burns), surgical trauma, accidental trauma, hemorrhagic shock and the like. The invention is also related to methods for preventing or reducing bacterial translocation, adult respiratory distress syndrome, adherence of blood cells and platelets to endothelial cells and pulmonary hypertension. In accordance with the present invention, these conditions are prevented or reduced by administering a dehydroepiandrosterone (DHEA) derivative as defined herein.

9 Claims, 9 Drawing Sheets

METHODS FOR PREVENTING PROGRESSIVE TISSUE NECROSIS, REPERFUSION INJURY, BACTERIAL TRANSLOCATION AND ADULT RESPIRATORY DISTRESS SYNDROME

CROSS-REFERENCE TO RELATED APPLICATIONS

The present application is a divisional of application Ser. No. 08/870,234, filed Jun. 5, 1997, now U.S. Pat. No. 5,977,095 which is a continuation-in-part of application Ser. No. 08/580,716 filed Dec. 29, 1995, now U.S. Pat. No. 5,753,640, and of application Ser. No. 08/516,540, filed Aug. 18, 1995, now U.S. Pat. No. 5,846,963. Application Ser. No. 08/580,716 is in turn a continuation-in-part application of Ser. No. 08/516,540, Ser. No. 08/516,540 is in turn a continuation -in-part application of Ser. No. 08/480,744, filed Jun. 7, 1995, now U.S. Pat. No. 5,587,369 application Ser. No. 08/480,745, filed Jun. 7, 1995, now U.S. Pat. No. 5,635,496 application Ser. No. 08/480,747, filed Jun. 7, 1995, now U.S. Pat. No. 5,811,418 and of application Ser. No. 08/480,748, filed Jun. 7, 1995, now U.S. Pat. No. 5,686,438 Ser. No. 08/480,744 is in turn a continuation-in-part of Ser. No. 08/284,688, filed Aug. 9, 1994, now U.S. Pat. No. 5,532,230 which in turn is a continuation-in-part of Ser. No. 08/029,442, filed Mar. 11, 1993, now abandoned. Each of these applications is incorporated herein by reference.

BACKGROUND OF THE INVENTION

The present invention is related to a method for preventing or reducing the effects of ischemia. The ischemia may be associated with injury or reperfusion injury, such as occurs as a result of infarctions, thermal injury (burns), surgical trauma, accidental trauma, hemorrhagic shock and the like. The invention is also related to methods for preventing or reducing bacterial translocation, adult respiratory distress syndrome, adherence of blood cells and platelets to endothelial cells and pulmonary hypertension. In accordance with the present invention, these conditions are prevented or reduced by administering a dehydroepiandrosterone (DHEA) derivative.

The publications and other materials used herein to illuminate the background of the invention, and in particular cases, to provide additional details respecting the practice, are incorporated by reference, and for convenience are numerically referenced in the following text and respectively grouped in the appended bibliography.

The consequences of accidental injury represent the leading causes of death in the United States among young adults. The use of aggressive resuscitation protocols has increased the chances of a patient surviving the initial trauma event following injury. However, the development of infectious complications still represents a significant problem in these individuals. Infection and the pathologic consequences of infection contribute significantly to the morbidity and mortality observed post-injury (1, 2). Post-surgical complications in particular, represent a frequently studied model of the array of systemic inflammatory aberrations observed following all types of severe traumatic injury and major surgery (2).

It is well known that trauma patients are predisposed to life-threatening infections as a consequence of being immunologically compromised (1, 2). It is believed that the negative influences on the immune system following severe traumatic injury are similar to the protective mechanisms involved in less severe injury. Recently, it has been established that the pathophysiology of trauma/shock injury is associated with an alteration in intestinal motility that can affect the ecology of the enteric microflora and contribute to bacterial translocation (3, 4). In addition, increase permeability of the intestinal capillaries facilitates infiltration of microbial toxins that induce a systemic inflammatory syndrome mediated by potent cytokines and other bioactive substances. One of the early indicators of the systemic inflammatory syndrome is induction of an acute phase response as measured by production of acute phase reactants (4, 5).

It appears that infection, leading to sepsis and multiple organ failure, remains a major hurdle to overcome in the pathophysiologic response to trauma (6, 7). Thus far, therapeutic modalities designed to either maintain or restore organ system homeostasis in surgical and trauma patients have only been partially successful, and for the most part disappointing. The failure to develop effective therapeutic drugs in this area may be due to an inadequate base of knowledge upon which past studies were designed. A better understanding is needed of the specific components of the physiologic response to traumatic and surgical injury, such as a better distinction between host-protective inflammatory mechanisms from those that are host-injurious.

A number of studies have shown that multiple alterations in immunity occur following stress and trauma. Changes in innate host resistance to infection (3, 4), loss of memory skin test reactions (7), altered cytokine production (8), decreased B-cell function (9), and profound deficits in T cell responses (10) are among the most notable. Significant monocytosis following trauma has also been observed, along with reduced monocyte/macrophage function and increased negative regulatory macrophage activity. These later observations are associated with an increased production of immunoregulatory E series prostaglandins (11). Likewise, serum immunoglobulin and protein profiles of patients appear to be significantly altered as a consequence of trauma (12, 13).

The existence of cytokine deficits/excesses following several distinct forms of traumatic injury have been established. These reports are relevant because lymphokines and cytokines are necessary and important for the induction and regulation of almost all types of immune responses (14). Recent studies have documented the existence of altered cytokine secretion in trauma patients, as a prolonged decrease in peripheral T cell potential for IL-2 secretion and IL-2R expression (15). Wood et al. demonstrated a persistent reduction in IL-2 production in vitro by PBMC from burn patients, with even lower levels of IL-2 production by T cells from burn patients suffering from systemic sepsis (10). Additionally, high levels of circulating soluble IL-2R in serum from trauma patients have been reported (10). A depression in yIFN production has been shown to occur in burned humans (16), as well as in mice (17). A number of investigators have noticed that iatrogenic procedures (surgical manipulations, transfusions, anesthesia) induce a marked depression in the capacity of activated T cells to produce IL-2 (18). There have also been observations of increased levels of tumor necrosis factor and IL-6 following burn and mechanical trauma (2, 6). These changes persisted for up to 21 days post injury (2,6). The persistence of plasma levels of IL-6 post-trauma appears to correlate with the severity and an unsuccessful outcome of septic episodes (6), and high levels of TNF have been associated with mortality (19). The cytokine, IL-6, is a potent biologic response modifier (20, for review). High blood levels have been correlated to a pathologic response to a variety of stress stimuli, such as inflammation or infection (20). IL-6 possesses a multiplicity of effects including induction of the acute phase response (21), ELAM expression on endothelial cells and growth of plasma cells (20). IL-6 can be produced by T cells, macrophages and fibroblasts in response to appropriate stimulation (20).

The metabolic and neuroendocrine responses to injury represent components of the adaptive stress response (22). Following a given stressful event, the production of many hepatic proteins (acute phase reactants) and neuroendocrine compound is altered. These changes are believed to enhance survivability of the host. Changes in liver function are marked by elevations in plasma $Zn^{2+}$, C-reactive protein, haptoglobin, α1-antitrypsin, fibrinogen, α1-acid glycoprotein and a number of heat-shock proteins. It is common to observe increased production of ACTH, cortisol and some neurotransmitters (beta-endorphin and eukephalins) with concomitant decreases in estrogen and androgen production (24,25). The altered production of many of these diverse substances can have pronounce effects. When an individual has an uneventful recovery from traumatic injury, neuroendocrine output and immune responsiveness will eventually return to normal (23, 24). In the patient sustaining severe injury, normal homeostasis of both the neuroendocrine and the immune systems become dysregulated for extended periods of time regardless of whether the patient recovers (18, 25).

Inflammatory stimuli such as thermal injury, major surgery and accidental trauma are know to be potent inducers of the HPA axis. The effect of activating the HPA is to alter normal adrenal output of steroid hormones, because glucocorticoid (GCS) production is increased at the expense of DHEAS synthesis and export. It has been clearly established that thermal injury of mice has a profound and reproducible effect on T cell function and host resistance (26). Specifically, it has been demonstrated that a number of T cell-derived lymphokines are either enhanced or repressed by the effect of thermal injury. These effects have led to the hypothesis that the change in GCS and DHEA levels is responsible for the alterations in innate and adaptive immune function. The mechanisms by which GCSs cause a depression of immunological function now appears to involve an interference with the function of certain nuclear transcription factors (27, 28). GCSs are now appreciated to exert a negative influence on gene transcription through the ability of GCS-receptor complexes to bind and inactivate the proto-oncogene product cJun, which combined with cFos activates the AP-1 transcription site (27, 28). Therefore, while the enhancement of gene transcription caused by GCS results from a classical DNA-protein interaction (29), repression of the transcription rate of other genes by this same hormone may result from specialized protein—protein (transcription factors-hormone-receptor complexes) interactions (27, 28).

Dehydroepiandrosterone (DHEA), a weak androgen, serves as the primary precursor in the biosynthesis of both androgens and estrogens (30). DHEA has been reported to play a mitigating role in obesity, diabetes, carcinogenesis, autoimmunity, neurological loss of memory (31–34), and the negative effects of GCS on IL-2 production by murine T cells (35).

Recent insight into the mechanism of action of DHEA has come from studies of ischemia-induced reperfusion injury. The clinical term used to describe the pathological process of wound extension is progressive dermal ischemia and it appears to represent the consequences of a host-initiated, time-dependent reperfusion injury. We questioned whether the degree of progressive dermal ischemia and necrosis of the skin following thermal injury in a murine model would be significantly reduced by post-burn, systemic administration of the steroid hormone DHEA (36).

DHEA and several related species of steroid hormones were evaluated for a capacity to either reduce or protect thermally injured mice against reperfusion damage of the microvasculature. Subcutaneous administration of DHEA at approximately 1–2 mg/kg/day achieved optimal protection. DHEA, as well as, 17α-hydroxy-pregnenolone, 16α-bromo-DHEA and androstenediol were all protective, whereas treatment of burned animals with other types of steroids, including androstenedione, 17β-estradiol or dihydrotestosterone had no protective effect. Additionally, intervention therapy with DHEA could be withheld for up to 4 hours after burn with substantial therapeutic benefit (36, 75). It is desired to identify additional compounds which could be used for protection of patients from reperfusion damage.

It has been observed that the immediate response to a burn injury is in many ways similar to an experiment reperfusion injury in other tissues. Studies suggest that DHEA, either directly or indirectly, through its action on endothelium prevents damage to the microvasculature in reperfusion injury.

In another study the effect of DHEA on ischemia/reperfusion injury of the isolated rat cremaster muscle was evaluated. The experimental approach employed intravital microscopy to establish whether DHEA pre-treatment of rats prior to ischemia/reperfusion of the isolated muscle would protect against damage to the capillaries and venules of microcirculation. These studies indicated that in control animals, 6 hours of ischemia followed by re-flow analysis at 90 minutes and 24 hours lead to insufficient perfusion of the muscle. In DHEA pre-treated rats, 6 hours of ischemia followed by re-flow analysis at 90 minutes, 24 hours and even 4 days showed normal perfusion values in the isolated muscle. In addition, it was clear that the DHEA pre-treatment prevented sticking of neutrophils to endothelium. Additional studies in a global ischemic model demonstrated the protective effect of DHEA given intravenously after resuscitation of clinically dead rats.

It has been recognized that the maintenance of vascular integrity is an important response to injury. Complex hemostatic mechanisms of coagulation, platelet function and fibrinolysis exist to minimize adverse consequences of vascular injury and to accelerate vascular repair. Vascular endothelial and smooth muscle cells actively maintain vessel wall thromboresistance by expressing several antithrombotic properties. When perturbed or injured, vascular cells express thrombogenic properties. The hemostatic properties of normal and perturbed vascular cells has been reviewed by Rodgers (38).

Interference with the supply of oxygenated blood to tissues is defined as ischemia. The effects of ischemia are known to be progressive, such that over time cellular vitality continues to deteriorate and tissues become necrotic. Total persistent ischemia, with limited oxygen perfusion of tissues, results in cell death and eventually in coagulation-induced necrosis despite reperfusion with arterial blood. Ischemia is probably the most important cause of coagulative necrosis in human disease. A substantial body of evidence claims that a significant proportion of the injury associated with ischemia is a consequence of the events associated with reperfusion of ischemic tissues, hence the term reperfusion injury. To place reperfusion injury into a clinical perspective, there are three different degrees of cell injury, depending on the duration of ischemia:

(1) With short periods of ischemia, reperfusion (and resupply of oxygen) completely restores the structural and functional integrity of the cell. Whatever degree of injury the cells have incurred can be completely reversed upon reoxygenation. For example, changes in cellular membrane potential, metabolism and ultrastructure are short-lived if the circulation is rapidly restored.

(2) With longer periods of ischemia, reperfusion is not associated with the restoration of cell structure and function, but rather with deterioration and death of cells. The response to reoxygenation in this case is rapid and intense inflammation.

(3) Lethal cell injury may develop during prolonged periods of ischemia, where reperfusion is not a factor.

The reversibility of cell injury as a consequence of ischemia is determined not only by the type and duration of the injury, but also by the cell target. Neurons exhibit very high sensitivity to ischemia, whereas myocardial, pulmonary, hepatic and renal tissues are intermediate in sensitivity. Fibroblasts, epidermis and skeletal muscle have the lowest susceptibility to ischemic injury, requiring several hours without blood supply to develop irreversible damage.

The proximity of the endothelium to circulating leukocytes makes it an important early target for neutrophil adherence and subsequent damage to vascular and parenchymal tissue. Interaction of activated endothelial cells and neutrophils is an immediate early, and necessary, event in ischemia/reperfusion injury (39, 40). The adhesive properties of endothelium are rapidly induced by the influx of oxygenated blood. In response to oxygen, endothelial cells become activated to produce several products, including leukotriene B4 (LTB4), platelet activating factor (PAF) and P-selectin. Leukotriene B4 is a potent neutrophil chemotactic agent (41, 42). Upon activation of the endothelial cells, P-selectin is rapidly translocated from intracellular organelles to the plasma membrane, where it acts to tether circulating neutrophils and stabilize them for activation by endothelial-bound PAF (platelet activating factor), endothelium-derived cytokines and other biologically active mediators (43). Thus, the physiologic interaction between the activated endothelium and the activated neutrophil is recognized as a critical and immediate early event in reperfusion injury of organs and tissues. Other cellular and biochemical mediators of inflammation injury such as platelets, the complement cascade, and the coagulation system are also important, but come into play much later in the cascade, in a process called coagulative necrosis. Finally, monocytes, macrophages, fibroblasts and smooth muscle cell infiltration are responsible for reconstruction and replacement of dead tissue with new, vital tissue, a process called wound healing.

A popular theory postulates a role for partially reduced, and thus activated, oxygen species in initiation of membrane damage in reperfusion injury. Present evidence indicates that activated oxygen (superoxide, peroxide, hydroxyl radicals) is formed during ischemic episodes and that reactive oxygen species injure ischemic cells. Toxic oxygen species are generated not during the period of ischemia itself, but rather on restoration of blood flow, or reperfusion. Two sources of activated oxygen species have been implicated as early events in reperfusion injury, those produced intracellularly by the xanthine oxidase pathway and those which can be transported to the extracellular environment by activated neutrophils (39, 40, 44–46).

In the xanthine oxidase-dependent pathway, purines derived from the catabolism of ATP during the ischemic period provide substrates for the activity of xanthine oxidase, which requires oxygen in catalyzing the formation of uric acid. Activated oxygen species are byproducts of this reaction. The species of oxygen radicals derived from the xanthine oxidase pathway are $O_2^-$ (superoxide with one electron) and $H_2O_2$ (hydrogen peroxide with two unpaired electrons). Superoxides are generated within the cytosol by xanthine oxidase (located in the cytosol). The superoxides are then catabolized to peroxides within mitochondria by superoxide dismutase. The peroxides are further converted to water either by glutathione peroxidase, in the cytosol, or by catalase in peroxisomes. Both glutathione peroxidase and catalase comprise the antioxidant defense mechanism of most cells. The major evidence for this hypothesis rests on the ability of allopurinol, an inhibitor of xanthine oxidase, to protect against reperfusion injury in experimental models.

In the NADPH-dependent pathway, NADPH oxidase is activated to generate superoxides through reduction of molecular oxygen at the plasma membrane. The superoxides are reduced to hydrogen peroxide by superoxide dismutase at the plasma membrane or within phagolysosomes. Finally, hydrogen peroxide within phagolysosomes can be reduced in the presence of superoxides or ferrous iron to hydroxyl radicals. A third form of oxygen metabolite is mediated by myloperoxidase in the presence of chlorine to reduce hydrogen peroxide to hypochlorous acid.

The hydroxyl radical is an extremely reactive species. Mitochondrial membranes offer a number of suitable substrates for attack by $OH^-$ radicals. The end result is irreversible damage to mitochondria, perpetuated by a massive influx of $Ca^{2+}$ ions. Another probable cause of cell death by hydroxyl radicals is through peroxidation of phospholipids in the plasma membrane. Unsaturated fatty acids are highly susceptible targets of hydroxyl radicals. By removing a hydrogen atom from fatty acids of cell membrane phospholipids, a free lipid radical is formed. These lipid radicals function like hydroxyl radicals to form other lipid peroxide radicals. The destruction of unsaturated fatty acids of phospholipids leads to a loss in membrane fluidity and cell death. Some investigators believe that the effects of oxidative stress cause programmed cell death in a variety of cell types.

Infarctions and traumatic injury involve many tissues, including vascular tissue. One response following traumatic injury is to shut down blood supply to the injured tissue. A purpose of this response is to protect the patient from the entry of infectious agents into the body. The severe reduction in blood supply is a main factor leading to progressive ischemia at the region of the traumatic injury. With progressive ischemia, tissue necrosis extends beyond the directly affected tissue to include surrounding unaffected tissue. This progressive ischemia plays an important role in defining the ultimate tissue pathology observed in humans as a consequence of the traumatic injury. For example, see Robson et al. (47).

One form of traumatic injury which has received a great deal of attention is thermal injury or burns. The burn wound represents a non-uniform injury, and the spectrum of injury ranges from tissue which is totally coagulated at the time of injury to tissue which is only minimally injured. Between these two extremes is tissue which is seriously damaged and not immediately destroyed, but which is destined to die. The etiology of the progressive depth of necrosis has been shown to be stasis and thrombosis of blood flow in the dermal vessels, causing ischemia and destruction of epithelial elements. This ischemia occurs for 24–48 hours following the thermal injury (47, 48). Many effects have been seen following a thermal injury, including adhesion of leukocytes to vessel walls, agglutination of red blood cells and liberation of vasoactive and necrotizing substances (48).

It has been established that burn-associated microvascular occlusion and ischemia are caused by the time dependent increase in development of microthrombi in the zone of stasis, a condition which eventually leads to a total occlusion of the arterioles and a microcirculatory standstill. Whereas margination of erythrocytes, granulocytes and platelets on venular walls are all apparent within the first few hours following thermal injury, the formation of platelet microthrombi (occurring approximately 24 hours after surgery) is believed to be responsible for creating the conditions that cause complete and permanent vascular occlusion and tissue destruction (49, 50). The formation of platelet microthrombi appears to provide the cellular basis for expanding the zone of complete occlusion and the ischemic necrosis that advances into the zone of stasis following thermal injury.

Bacterial translocation is the process by which indigenous gut flora penetrate the intestinal barrier and invade sterile tissue. Included in this process is the migration of microbial organisms to the draining mesenteric lymph nodes, spleen, liver, blood and in some instances, the lung (51, 52). This phenomenon has been documented in humans following thermal injury (53–55) and ischemia-reperfusion injury (56). DHEA has been reported to be useful in reducing or preventing bacterial translocation (36, 75). It is desired to identify additional compounds which are useful for preventing or reducing bacterial translocation.

The evidence implicating the role of neutrophils in adult respiratory distress syndrome (ARDS) is substantial but indirect (57). Some of the first suggestions that neutrophils may cause an ARDS-like picture were found in severely neutropenic patients who were infused intravenously with donor neutrophils. Occasionally, within hours of neutrophil infusion, there was an abrupt "white-out" of the lungs (by x-ray) and onset of ARDS symptoms. Numerous studies have shown that neutrophils accumulate in the lung during ARDS. For example, their presence has been demonstrated histologically. During the early phases of ARDS, the number of circulating whole blood cells transiently decreases, probably due to their abnormal pulmonary sequestration. Some neutrophils that accumulate within lung capillaries leave the vascular space and migrate into the interstitium and alveolar airspaces. In normal healthy volunteers, neutrophils account for less than 3% of the cells that can be obtained by bronchoalveolar lavage (BAL). In patients with ARDS, the percentage of neutrophils in the lavage is markedly increased to 76–85%. The accumulation of neutrophils is associated with evidence of their activation. They demonstrate enhanced chemotaxis and generate abnormally high levels of oxygen metabolites following in vitro stimulation. Elevated concentrations of neutrophil secretory products, such as lactoferrin, have been detected in the plasma of patients with ARDS. Further evidence that neutrophils actively participate in lung injury was obtained from a clinical study of patients with mild lung injury who were neutropenic for an unrelated reason (e.g., receiving chemotherapy). It was noted that lung impairment frequently worsened if a patient's hematological condition improved and circulating neutrophil counts recovered to normal levels.

Although the evidence implicating neutrophils in the genesis of human ARDS is still largely indirect, data demonstrating the importance of neutrophils in various animal models of acute lung injury is convincing. The common approach that has been used to demonstrate neutrophil independence is to deplete the animal of circulating neutrophils and measure any diminution in lung injury that occurs. Although a number of experimental models have been used to study neutrophil dependence of lung injury, only a few have been selected for discussion herein because of space limitations.

One extensively studied model is the administration of endotoxin to sheep. When endotoxin is intravenously infused into sheep, a complex set of events occurs, one of which is increased permeability of the pulmonary capillary endothelium. This is manifested by an increase in the flow of lung lymph which contains a higher-than-normal protein concentration. These changes indicate a reduction in the ability of the capillary endothelium to retain plasma proteins within the vascular space. The neutrophil dependence of the permeability injury was established when it was found that neutrophil depletion of the sheep prior to endotoxin infusion protected them. Another in vitro model of acute lung injury involves intravenous infusion of cobra venom factor into rats, which causes complement activation followed by leukoaggregation and sequestration of neutrophils within the pulmonary microvasculature. Alveolar wall damage occurs, leading to interstitial and intra-alveolar edema with hemorrhage and fibrin deposition. Again, neutrophil depletion prevented the increased pulmonary capillary leak.

Isolated, perfused rabbit or rat lungs have also been used to study mechanisms of alveolar injury under circumstances that allow improved control of the variables that affect fluid flux. When neutrophils were added to the perfusate and then stimulated, albumin leaked from the vascular compartment into the lung interstitium and alveolar airspaces. Unstimulated neutrophils or stimulus alone (e.g., phorbol myristate acetate) failed to increase alveolar-capillary permeability.

As further proof that stimulated neutrophils can independently injure lung tissue, in vitro experiments have been performed using vascular endothelial and lung epithelial cells as targets. In some reports, neutrophils have been shown to detach endothelial cells or alveolar epithelial cells from the surface of the tissue culture dish. Obviously, if such an event were to occur in vivo, the denuded surfaces would permit substantial leakage of plasma contents. Furthermore, many reports have provided clear evidence that stimulated neutrophils are able to facilitate lysis of cultured vascular endothelial cells and alveolar epithelial cells. DHEA has been reported to be useful in reducing or preventing ARDS (36, 75). It is desired to identify additional compounds which are useful for preventing or reducing ARDS.

In the United States, chronic obstructive pulmonary disease (COPD) represents the fifth most common cause of death (58). COPD also constitutes one of the most important causes of work incapacity and restricted activity (59). COPD, along with many other pulmonary diseases, causes pulmonary hypertension and right ventricular hypertrophy or cor pulmonale. Over 12 million patients in the United States alone have chronic bronchitis or emphysema, and approximately 3 million are chronically hypoxic with $PaO_2 < 60$ mmHg. These patients develop hypoxic pulmonary vasoconstriction, and eventually, right ventricular hypertrophy (60). Once right ventricular hypertrophy develops, the three-year mortality rate of those patients is 60% (61, 62). Irrespective of the current management, morbidity and mortality of patients with COPD and pulmonary hypertension remain high.

One model to study pulmonary hypertension is the pulmonary vasoconstriction induced by alveolar hypoxia.

Experiments in isolated animal (63) and human (64) pulmonary arteries suggest that hypoxia-induced pulmonary vasoconstriction is mediated by a direct effect of hypoxia on pulmonary vascular smooth muscle cell. It has been reported (65) that hypoxia can depolarize the pulmonary vascular smooth muscle membrane by inducing an increase in tissue Na+ and a decrease in K+. More recently, it has been reported that hypoxia can alter the membrane potential in rat main pulmonary artery smooth muscle cell and can stimulate $Ca^{2+}$ influx through voltage-gated channels (66). There is strong evidence that $Ca^{2+}$ entry blockade can attenuate hypoxic pulmonary vasoconstriction in isolated rat lung (67) and in patients with chronic obstructive lung disease (68). Conceivably, hypoxia may effect other membrane transport mechanisms that are involved in $Ca^{2+}$ influx and/or efflux. For example, Voelkel et al. (69) speculated that hypoxia may impair $Ca^{2+}$ extrusion. Farrukh et al. (70) has demonstrated that cAMP and cGMP reverse hypoxic pulmonary vasoconstriction by stimulating $Ca^{2+}$ ATP-ase-dependent $Ca^{2+}$ extrusion and/or redistribution. It is desired to identify compounds which are useful for treating, reducing or preventing pulmonary hypertension.

DHEA is an endogenous androgenic steroid which has been shown to have a myriad of biological activities. Araneo et al. (26) has shown that the administration of DHEA to burned mice within one hour after injury resulted in the preservation of normal immunologic competence, including the normal capacity to produce T-cell-derived lymphokines, the generation of cellular immune responses and the ability to resist an induced infection. Eich et al. (71, 72) describes the use of DHEA to reduce the rate of platelet aggregation and the use of DHEA or DHEA-sulfate (DHEA-S) to reduce the production of thromboxane, respectively.

Nestler et al. (73) shows that administration of DHEA was able in human patients to reduce body fat mass, increase muscle mass, lower LDL cholesterol levels without affecting HDL cholesterol levels, lower serum apolipoprotein B levels, and not affect tissue sensitivity to insulin. Kent (74) reported DHEA to be a "miracle drug" which may prevent obesity, aging, diabetes mellitus and heart disease. DHEA was widely prescribed as a drug treatment for many years. However, the Food and Drug Administration recently restricted its use. DHEA is readily interconvertible with its sulfate ester DHEA-S through the action of intracellular sulfatases and sulfotransferases.

Daynes et al. (75) shows that administration of DHEA was useful for the reducing or preventing progressive tissue necrosis, reperfusion injury, bacterial translocation and adult respiratory distress syndrome. However, Daynes et al. (75) further shows that the administration of DHEAS was not useful for reducing or preventing these pathological conditions.

Despite the above teaching of Daynes et al. (75), it has now been discovered that DHEAS can be used to reduce or prevent the pathophysiologic responses to the above noted pathological conditions when administered intravenously when necessary or orally at the doses described in detail below. It has also now been discovered that additional DHEA congeners can be used to reduce or prevent the pathophysiologic responses to the above noted pathological conditions.

SUMMARY OF THE INVENTION

The present invention is directed to a method for preventing or reducing reperfusion injury following ischemia, cellular damage associated with ischemic episodes, such as infarction, traumatic injury or hemorrhagic shock, and thus to prevent or reduce the consequent progressive necrosis of tissue associated with such ischemia. The present invention is also directed to a method for preventing or reducing bacterial translocation. The present invention is further directed to a method for preventing or reducing ARDS. The present invention is also directed to a method for inhibiting the expression of p-selectin on endothelium. Finally, the present invention is directed to a method for preventing or reducing pulmonary hypertension. Reperfusion injury is prevented or reduced by administering a dehydroepiandrosterone (DHEA) derivative to a patient following, e.g., an infarction, traumatic injury hemorrhagic shock or the like. Similarly, bacterial translocation is prevented or reduced in a patient by administering a DHEA derivative. ARDS is also prevented or reduced in a patient by administering a DHEA derivative. Similarly, p-selectin expression by the endothelium is prevented or reduced in a patient by administering a DHEA derivative. Similarly, pulmonary hypertension is prevented or reduced in a patient by administering a DHEA derivative.

DETAILED DESCRIPTION OF THE INVENTION

Figure 1:
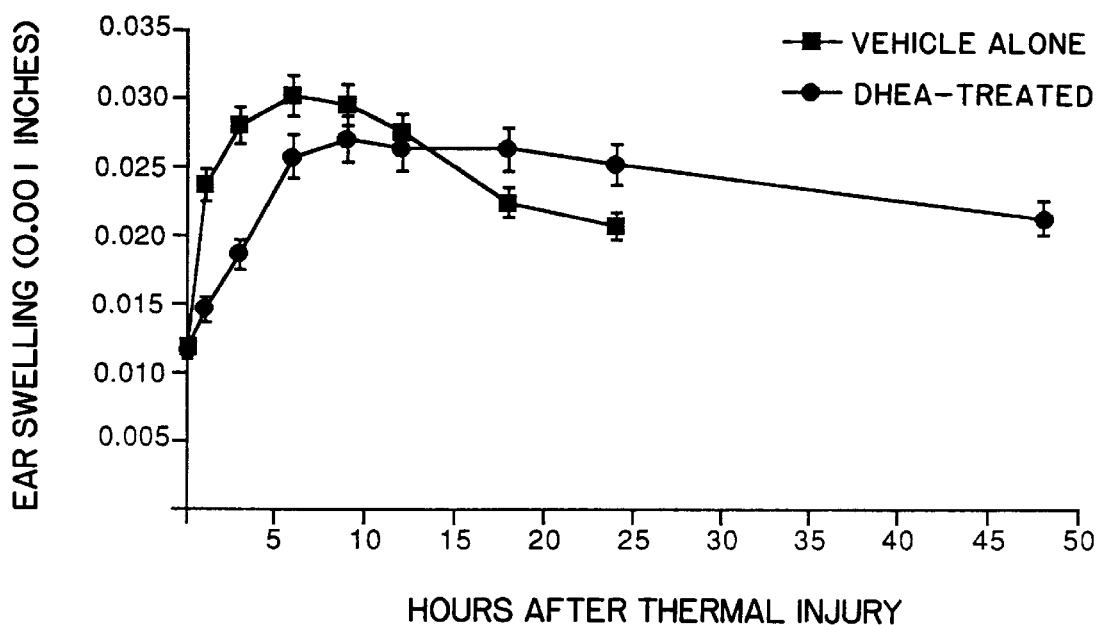
FIG. 1 shows the results of the analysis of edema formation (ear swelling) and resolution in the burned ears of control and DHEA-treated mice.

The present invention is directed to a method for preventing or reducing reperfusion injury following ischemia, and cellular damage associated with ischemic episodes, such as infarction, traumatic injury or hemorrhagic shock. An example of an infarction is a myocardial infarction. Examples of traumatic injury include thermal injury, surgery, chemical burns, blunt trauma or lacerations and the like. By preventing or reducing reperfusion injury following ischemia and cellular damage associated with ischemic episodes, the consequent progressive necrosis of tissue associated with such infarction or injury is also prevented or reduced. In accordance with the present invention, reperfusion injury or cellular damage associated with ischemic episodes, such as infarction, traumatic injury hemorrhagic shock or the like, is prevented or reduced by administering a dehydroepiandrosterone (DHEA) derivative intravenously to a patient as early as possible, preferably within six hours, more preferably within four hours, and most preferably within two hours, of the ischemia, infarction traumatic injury, hemorrhagic shock or the like.

The present invention is also directed to a method for preventing or reducing bacterial translocation. In accordance with the present invention, bacterial translocation is prevented or reduced in a patient by administering a DHEA derivative as described above. The DHEA derivative is administered within 24 hours of an injury in which bacterial translocation is one of the sequelae.

The present invention is also directed to a method for preventing or reducing adult respiratory distress syndrome (ARDS). In accordance with the present invention, ARDS is prevented or reduced in a patient by administering a DHEA derivative as described above. The DHEA derivative congener is administered prior to clinical symptoms of ARDS, primarily to individuals at risk for ARDS. Alternatively, the DHEA derivative can be administered orally to patients at risk for ARDS.

The present invention is also directed to a method for preventing or reducing pulmonary hypertension. In accordance with the present invention, pulmonary hypertension is prevented or reduced in a patient by administering a DHEA derivative as described above. The DHEA is derivative is administered to patients showing signs of pulmonary hypertension within 24 hours of events which could lead to alveolar hypoxia.

Examples of a DHEA derivative, include but are not limited to, compounds having the general formulas I and II and their pharmaceutically acceptable salts

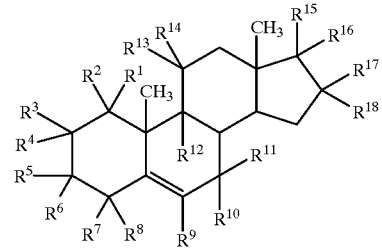

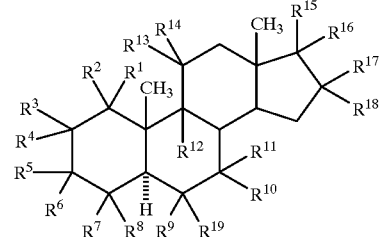

wherein
$R^1, R^2, R^3, R^4, R^6, R^7, R^8, R^9, R^{10}, R^{11}, R^{12}, R^{13}, R^{14}$ and $R^{19}$ are independently H, —OH, halogen, $C_{1-10}$alkyl or $C_{1-10}$alkoxy;

$R^5$ is H, —OH, halogen, $C_{1-10}$alkyl, $C_{1-10}$alkoxy or $OSO_2R^{20}$;

$R^{15}$ is
(1) H, halogen, $C_{1-10}$alkyl or $C_{1-10}$alkoxy when $R^{16}$ is —C(O)OR$^{21}$ or
(2) H, halogen, OH or $C_{1-10}$ alkyl when $R^{16}$ is H, halogen, OH or $C_{1-10}$ alkyl or
(3) H, halogen, $C_{1-10}$ alkyl, $C_{1-10}$ alkenyl, $C_{1-10}$ alkynyl, formyl, $C_{1-10}$ alkanoyl or epoxy when $R^{16}$ is OH; or
$R^{15}$ and $R^{16}$ taken together are =O;

$R^{17}$ and $R^{18}$ are independently
(1) H, —OH, halogen, $C_{1-10}$ alkyl or $C_{1-10}$ alkoxy when $R^{16}$ is H, OH, halogen, $C_{1-10}$ alkyl or —C(O)OR$^{21}$ or
(2) H, ($C_{1-10}$ alkyl)$_n$amino, ($C_{1-10}$ alkyl)$_n$amino-$C_{1-10}$ alkyl, $C_{1-10}$ alkoxy, hydroxy-$C_{1-10}$ alkyl, $C_{1-10}$ alkoxy-$C_{1-10}$ alkyl, (halogen)$_m$-$C_{1-10}$ alkyl, $C_{1-10}$ alkanoyl, formyl, $C_{1-10}$ carbalkoxy or $C_{1-10}$ alkanoyloxy when $R^{15}$ and $R^{16}$ taken together are =O; or $R^{17}$ and $R^{18}$ taken together are =O or taken together with the carbon to which they are attached form a 3–6 member ring containing 0 or 1 oxygen atom; or $R^{15}$ and $R^{17}$ taken together with the carbons to which they are attached form an epoxide ring;

$R^{20}$ is OH, pharmaceutically acceptable ester or pharmaceutically acceptable ether;

$R^{21}$ is H, (halogen)$_m$-$C_{1-10}$ alkyl or $C_{1-10}$ alkyl;

n is 0, 1 or 2; and m is 1, 2 or 3, with the provisos that
(a) $R^3$ is not H, OH or halogen when $R^1, R^2, R^4, R^6, R^7, R^9, R^{10}, R^{12}, R^{13}, R^{14}, R^{17}$ and $R^{19}$ are H and $R^5$ is OH or $C_{1-10}$ alkoxy and $R^8$ is H, OH or halogen and $R^{11}$ is H or OH and $R^{18}$ is H, halogen or methyl and $R^{15}$ is H and $R^{16}$ is OH;

(b) $R^3$ is not H, OH or halogen when $R^1, R^2, R^4, R^6, R^7, R^9, R^{10}, R^{12}, R^{13}, R^{14}, R^{17}$ and $R^{19}$ are H and $R^5$ is OH or $C_{1-10}$ alkoxy and $R^8$ is H, OH or halogen and $R^{11}$ is H or OH and $R^{18}$ is H, halogen or methyl and $R^{15}$ and $R^{16}$ taken together are =O;

(c) $R^5$ is not H, halogen, $C_{1-10}$ alkoxy or $OSO_2R^{20}$ when $R^1$, $R^2$, $R^3$, $R^{4,}$ $R^6$, $R^7$, $R^8$, $R^9$, $R^{10}$, $R^{12}$, $R^{13}$, $R^{14}$ and $R^{17}$ are H and $R^{11}$ is H, halogen, OH or $C_{1-10}$ alkoxy and $R^{18}$ is H or halogen and $R^{15}$ and $R^{16}$ taken together are =O; and (d) $R^5$ is not H, halogen, $C_{1-10}$ alkoxy or $OSO_2R^{20}$ when $R^1$, $R^2$, $R^3$, $R^4$, $R^6$, $R^7$, $R^8$, $R^9$, $R^{10}$, $R^{12}$, $R^{13}$, $R^{14}$ and $R^{17}$ are H and $R^{11}$ is H, halogen, OH or $C_{1-10}$ alkoxy and $R^{18}$ is H or halogen and $R^{15}$ is H and $R^{16}$ is H, OH or halogen.

Compounds of general formulas I and II are synthesized as described in U.S. Pat. Nos. 4,898,694; 5,001,119; 5,028,631; and 5,175,154, incorporated herein by reference. The compounds represented by the general formulas I and II exist is many stereoisomers and these formulas are intended to encompass the various stereoisomers. Examples of representative compounds which fall within the scope of general formulas I and II included the following:

5α-androstan-17-one;
16α-fluoro-5α-androstan-17-one;
3β-methyl-5α-androsten-17-one;
16α-fluoro-5α-androstan-17-one;
17β-bromo-5-androsten-16-one;
17β-fluoro-3β-methyl-5-androsten-16-one;
17α-fluoro-5α-androstan-16-one;
3β-hydroxy-5-androsten-17-one;
17α-methyl-5α-androstan-16-one;
16α-methyl-5-androsten-17-one;
3β,16α-dimethyl-5-androsten-17-one;
3β,17α-dimethyl-5-androsten-16-one;
16α-hydroxy-5-androsten-17-one;
16α-fluoro-16β-methyl-5-androsten-17-one;
16α-methyl-5α-androstan-17-one;
16-dimethylaminomethyl-5α-androstan-17-one;
16β-methoxy-5-androsten-17-one;
16α-fluoromethyl-5-androsten-17-one;
16-methylene-5-androsten-17-one;
16-cyclopropyl-5α-androstan-17-one;
16-cyclobutyl-5-androsten-17-one;
16-hydroxymethylene-5-androsten-17-one;
3α-bromo-16α-methoxy-5-androsten-17-one;
16-oxymethylene-5-androsten-17-one;
3β-methyl-16ξ-trifluoromethyl-5α-androstan-17-one;
16-carbomethoxy-5-androsten-17-one;
3β-methyl-16β-methoxy-5α-androstan-17-one;
3β-hydroxy-16α-dimethylamino-5-androsten-17-one;
17α-methyl-5-androsten-17β-ol;
17α-ethynyl-5α-androstan-17β-ol;
17β-formyl-5α-androstan-17β-ol;
20,21-epoxy-5α-pregnan-17α-ol;
3β-hydroxy-20,21-epoxy-5α-pregnan-17α-ol;
16α-fluoro-17α-ethenyl-5-androsten-17β-ol;
16α-hydroxy-5-androsten-17α-ol;
16α-methyl-5α-androstan-17α-ol;
16α-methyl-16β-fluoro-5α-androstan-17α-ol;
16α-methyl-16β-fluoro-3-hydroxy-5-androsten-17α-ol;
3β,16β-dimethyl-5-androsten-17β-ol;
3β,16,16-trimethyl-5-androsten-17β-ol;
3β,16,16-trimethyl-5-androsten-17-one;
3β-hydroxy-4α-methyl-5-androsten-17α-ol;
3β-hydroxy-4α-methyl-5-androsten-17-one;
3α-hydroxy-1α-methyl-5-androsten-17-one;
3α-ethoxy-5α-androstan-17β-ol;
5α-pregnan-20-one;
3β-methyl-5α-pregnan-20-one;
16α-methyl-5-pregnen-20-one;
16α-methyl-3β-hydroxy-5-pregnen-20-one;
17α-fluoro-5-pregnen-20-one;
21-fluoro-5α-pregnan-20-one;
17α-methyl-5-pregnen-20-one;
20-acetoxy-cis-17(20)-5α-pregnene;
3α-methyl-16,17-epoxy-5-pregnen-20-one.

It is known that reperfusion injury, hemorrhagic shock, infarctions and traumatic injury, such as myocardial infarctions, burns, major surgery, chemical burns, blunt trauma, lacerations and the like, can lead to injury in which tissue necrosis extends beyond the directly affected tissue to include surrounding unaffected tissue. This ischemia plays an important role in defining the ultimate tissue pathology observed as a consequence of traumatic injury in humans (47). It is also known that one consequence of thermal injury is bacterial translocation. Thermal injury, i.e., burns, is the best studied traumatic injury in which progressive ischemia occurs.

The loss of viable skin through the process of progressive ischemic necrosis contributes significantly to much of the skin loss that requires surgical grafting following burn injury (76). A number of animal models have been developed which mimic very closely many aspects of clinical burns. For example, following the administration of an experimental full-thickness scald burn which covers >20% of the total body surface area to rodents (e.g. 72° C.) hot water exposure for 7 seconds), the immediate tissue effects of the burn injury appear quite moderate, compared to the extensive damage to the affected and surrounding skin tissue which develops over the subsequent 24–72 hour period. Thus, it has been observed in both clinical and experimental burns that the total amount of skin lost to a severe thermal injury represents the sum of the immediate direct tissue destruction plus the latent damage that occurs to the epidermis, dermis and inclusive skin structures of the affected and surrounding skin areas.

Initial investigations using the dorsal skin thermal injury model in rodents led to some dramatic findings. It was discovered that scald burn-injured mice that are treated within one hour after thermal injury with the weakly androgenic steroid hormone, dehydroepiandrosterone (DHEA), develop and resolve their wounds in a manner quite distinct from untreated or sham treated thermally injured controls. By 3–4 days after thermal injury, all control-injured animals demonstrate third and fourth degree damage to the vast majority of skin tissue within the injury site. Virtually all of the skin within the affected area is ultimately lost as a consequence of progressive ischemic necrosis. The extent of tissue damage in these animals associates with a major loss in skin structures (hair follicles, blood vessels, neurons, and sebaceous glands), an infiltration of fibroblasts, extensive wound contraction, and the formation of numerous fibrous adhesions under the affected skin area. The DHEA-treated animals (about 2 mg/kg/day after an initial loading dose of 4 mg/kg), however, are observed to develop significantly less pathology, with much less evidence of progressive damage to the dermis, subdermis and associated skin structures. While re-epithelialization is active in both the burn control and the DHEA-treated injured groups of mice, DHEA-treated mice demonstrate much less wound contraction with notably less formation of fibrous adhesions underlying the wound site.

With the use of the dorsal skin injury model, it was clearly demonstrated that DHEA treatment exerts a very positive influence on wound progression. These findings suggested that treatment of thermally injured animals with DHEA may influence wound healing based on a fundamental capacity to prevent ischemia. Consequently, a modification of the procedure first described by Boykin et al. (50) and Eriksson et al. (77) was developed to permit a kinetic evaluation and quantification of progressive dermal ischemia during the immediate and later phases of thermally-injured mouse ears. The technique employed in these studies facilitated a rigorous and sequential monitoring of the time-dependent progression of tissue damage and ischemic necrosis in mouse ears subjected to a hot water scald burn (52° C. for 24 seconds), and has become a valid animal model for investigating progressive ischemia of burn-injured tissue.

The mouse ear consists of two layers of skin, cartilage, sparse muscle cells and connective tissue. Organization of the ear vasculature is well-ordered, comprised of arterioles, precapillary arterioles, post-capillary venules and venules. Employing an apparatus capable of administering controlled thermal injury to the entire surface area of the mouse ear, researchers have reported observing an immediate change in blood flow patterns. As a result of precise morphological studies on hemodynamic changes following burn injury of the mouse ear, three distinct zones, easily separable by the degree of pathology, have been described. These zones comprise the zone of complete capillary occlusion, the zone of partial occlusion (stasis), and the zone of capillary hyperemia (50). By one hour after injury, the area of total capillary occlusion is restricted to the distal margin of the mouse ear. Located more proximally to this outermost, and immediately sensitive area, is the zone of partial occlusion or stasis. It is this major area of ear tissue which becomes progressively ischemic over the 24–72 hour period following thermal injury, and which ultimately undergoes necrosis. Finally, the most proximal area of the affected ear is the zone of hyperemia. This area is fairly resistant to progressive post-burn ischemia.

It has been discovered that the administration to a patient of a therapeutically effective amount of DHEA, DHEAS, a DHEA congener or a DHEA derivative as defined by general formulas I and II above in a physiologically acceptable carrier as early as possible, preferably within four hours of a reperfusion injury, hemorrhagic shock, infarction or traumatic injury, results in the prevention or the reduction of reperfusion injury, hemorrhagic shock, infarction or traumatic injury-associated ischemia. The prevention or reduction of the ischemia results in prevention or reduction of the consequent necrosis of tissue associated with such ischemia. This reduction in ischemia results from the reduction of adherence of neutrophils to endothelial cells, as shown in the Examples. As a consequence of the reduced neutrophil adherence, the neutrophils do not become activated and do not produce cellular factors which lead to platelet aggregation. It is most preferred that the DHEA derivative be administered within two hours of the patient's sustaining the reperfusion, hemorrhagic shock, infarction or traumatic injury. The DHEA derivative is administered to patients in other pharmaceutically acceptable form and within binders, elixirs or other pharmaceutically acceptable mixtures, or with other pharmaceutically acceptable carriers. The DHEA derivative is administered by intravenous injection. Subsequent doses of a DHEA derivative can be administered intravenously or orally. If the DHEA deriviative is administered prior to tissue injury, such as to a patient prior to surgery, the DHEA derivative can also be administered orally.

The physiological effects of DHEA in these similar yet different models of reperfusion injury have directed research towards an endothelial cell target. In the reperfusion studies it is the microcirculatory endothelium of the skin and muscle. In the hemorrhagic shock studies described in detail below, in which the focus is directed towards the protective effects of DHEA, DHEAS, DHEA congeners or the DHEA derivatives of general formulas I and II on the pathology associated from hemorrhagic shock, it is the microcirculatory endothelium of the gut. The gut endothelium plays a critical target in surgical shock/trauma, as it carries the responsibility of maintaining gut barrier function. Intervention with intravenous DHEA, DHEAS, a DHEA congener or a DHEA derivative at specific times following resuscitation from hemorrhagic shock reduces or even prevents a pathophysiologic response. The Examples below demonstrate that DHEA or DHEAS intervention significantly reduces morbidity and mortality following a surgical shock/trauma in mice. Similar results are obtained with the compounds of general formula I or general formula II, set forth above.

The change in steroid hormone levels evoked by abdominal surgery with hemorrhagic shock and resuscitation may contribute to the pathophysiologic response displayed during the post-operative period. Stress-induced elevations in plasma GCS levels that subsequently regulate circulating levels of DHEAS, may be a significant factor involved in the alterations of host resistance to infection. Complications caused by the transport of soluble toxins and translocation of opportunistic pathogens that are normal inhabitants of the gut are even more life-threatening because of their prevalence and ready access to host tissue. Administration of DHEAS prevents or reduces many of these pathophysiologic responses.

Pharmaceutical compositions containing a DHEA derivative as the active ingredient in intimate admixture with a pharmaceutical carrier can be prepared according to conventional pharmaceutical compounding techniques. The carrier may take a wide variety of forms depending on the form of preparation desired for administration, e.g. intravenous or oral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). If desired, tablets may be sugar-coated or enteric-coated by standard techniques. The carrier may comprise sterile water, although other ingredients, for example, to aid solubility or for preservative purposes, may be included. Injectable suspensions may also be prepared, in which case appropriate liquid carriers, suspending agents and the like may be employed.

The dose of the DHEA derivative congener is based on well known pharmaceutically acceptable principles to deliver a DHEA equivalent dose of, e.g., 1–200 mg/kg, preferably 2–50 mg/kg. Generally the dose of DHEA derivative necessary to deliver this level of DHEA dose or DHEA eqivalent dose is 1–1000 mg/kg, preferably 2–500 mg/kg, more preferably 2–200 mg/kg. Alternatively, the dosage of DHEA derivative utilized will deliver an equivalent of 10–100 mg/kg of DHEA. The dose of DHEA derivative necessary to deliver this level of DHEA dose or DHEA equivalent dose is 10–1,000 mg/kg, preferably 50–800 mg/kg, more preferably, 100–500 mg/kg. The dose of DHEA derivative can be readily determined using conventional methods and will generally be in the range of the doses specified for DHEAS. For unprotected compounds, i.e., those which can be sulfated by human sulfotransferases or sulfatases, it is preferred to administer an excess dose to insure that sufficient active agent is administered, especially if sulfatases are not active at the site of tissue injury. The patient is treated with a DHEA derivative for 3–30 days, preferably 7–14 days, following the infarction, hemorrhagic shock or traumatic injury.

For those patients who are at high risk for a myocardial infarction or at risk for reperfusion injury, it is possible to prevent or reduce progressive ischemia associated with such an infarction or reperfusion injury by administering a DHEA derivative prior to, simultaneously and/or following infarction, hemorrhagic shock or reperfusion injury in the dosages described above. Intravenous treatment with a DHEA derivative following myocardial infarction is as described above. The DHEA derivative can be administered to such a patient who demonstrates classical signs for an imminent myocardial infarction in the same manner as described above, for treatment following such an infarction. Alternatively, the DHEA derivative congener can be administered orally for those patients at risk.

For those patients who are at risk of bacterial translocation, such bacterial translocation is prevented or reduced by administering a DHEA derivative as described above in the dosages described above. The administration to prevent or reduce bacterial translocation continues until the patient is no longer at risk for the bacterial translocation.

It has been discovered that it is critical that the DHEA derivative be administered soon after reperfusion injury, hemorrhagic shock, infarction or traumatic injury in order to prevent or reduce any cellular damage. If the administration of these compounds occurs too late, blood vessels will become occluded (initially with neutrophils adhering to endothelial cells), at which point the administration of these compounds will be unable to prevent or reduce the ischemia. The time frame within which the administration should begin may be dependent on the type of reperfusion injury, infarction or traumatic injury, and can be readily determined by appropriate animal models. However, it is preferred that administration of DHEA derivative commence within four hours, and most preferably within two hours of the ischemia, hemorrhagic shock, infarction or traumatic injury. The administration of DHEA derivative to prevent or reduce bacterial translocation should begin within 24 hours of the injury or stress-causing event. It is preferred that administration of these compounds to prevent or reduce bacterial translocation begin within four hours, and most preferably within two hours.

ARDS is prevented or reduced by administering a DHEA derivative as described above, in the dosage described above. The administration of a DHEA derivative to reduce the adherence of blood cells and platelets to endothelial cells by reducing the expression of p-selectin is as described above as to dose and mode of administration, i.e., intravenously or orally, depending on the timing of the administration relative to the need to reduce the adhesion. The administration of a DHEA derivative to prevent or reduce ARDS should begin before the onset of clinical symptoms. Generally, a DHEA derivative will be administered to patients at risk of ARDS. In this case, the DHEA derivative can be administered orally as well.

Pulmonary hypertension is prevented or reduced by administering a DHEA derivative as described above, in the dosage described above. Generally, the DHEA derivative will be administered to patients at risk of pulmonary hypertension. In this case, the DHEA derivative can be administered orally as well.

The present invention is described by reference to the following Examples, which are offered by way of illustration and are not intended to limit the invention in any manner. Standard techniques well known in the art or the techniques specifically described below were utilized.

EXAMPLE 1

Experimental Thermal-Injury Model

An experimental thermal injury model employing mouse ears was developed where temperature and exposure time were established empirically. The conditions represented the minimal burn injury which progressed to total tissue necrosis in the exposed ear of untreated mice by 24–72 hours post-burn. Groups of Balb/c mice, approximately nine weeks old, were given an identifying mark, and then divided into control and treated subgroups. The thickness of the ear to be immersed in hot water was recorded, and then the entire ear of the anesthetized mouse was dipped into 52° C. water for exactly 24 seconds. Each mouse was returned to its cage after an injection of either the propylene glycol vehicle (control) or 100 mg of test agent dissolved in propylene glycol. Ear swelling changes were monitored on individual mice at pre-burn, and at various hours after thermal injury.

EXAMPLE 2

Effect of DHEA in the Thermal-Injury Model

Groups of Balb/c mice, approximately 9 weeks old, were given an identifying mark, and then divided into control and treated subgroups. The thickness of the ear to be immersed in hot water was recorded, and then the entire ear of the anesthetized mouse was dipped into 52° C. water for exactly 24 seconds. Each mouse was returned to its cage after an injection of either the propylene glycol vehicle (control) or 100 mg of DHEA agent dissolved in propylene glycol. Ear swelling changes were monitored on individual mice at pre-burn, and at 1, 3, 6, 9, 12, 18, 24 and 48 hours after thermal injury.

The results of the analysis of edema formation and resolution in the ears of control and DHEA-treated mice are shown in FIG. 1. Ear swelling, as a measure of edema, reached a peak in both DHEA-treated and untreated burned mice by six hours after injury. In the untreated group, the extent of swelling started to decline within 12 hours, and continued to decline rapidly over the subsequent 12 hour periods. Between 24 and 48 hours post-burn, ear measurements had to be discontinued in the untreated group due to the complete loss of ear tissue resulting from the complete micro-vascular occlusion of the original zone of stasis. The kinetic analysis of edema in untreated and DHEA-treated thermally-injured mice showed that the events which take place during the first 24 hours following a burn-induced injury are critical to the viability of the thermally-injured tissue, such that the eventual preservation of viable ear tissue at 48 hours correlates inversely with the rate at which the swelling response recedes between the peak at six hours and the final 48 hour time period.

In addition to the analysis of edema in untreated and DHEA-treated thermally-injured mice, the changes in viability of the ear tissue itself were documented photographically. Injury of the ear tissue in mice given only the vehicle was extensive, with greater than 70% of the ear tissue being necrotic and destroyed within 48 hours. The total affected area appeared to encompass both the zone of complete vascular occlusion and the original zone of stasis. This latter zone became damaged as a secondary consequence of thermal injury, a condition which defines progressive post-burn dermal ischemia. However, DHEA-treated mice showed little injury and the preservation of burned ear tissue that was markedly affected by, but not lost to the effects of thermal injury corresponded to only the original zone of complete vascular occlusion.

EXAMPLE 3

Effect of Various Compounds in the Thermal Injury Model

Groups of nine-week old thermally injured Balb/c mice were divided into subgroups given either vehicle alone, DHEA, androstenediol, 16β-bromo-DHEA, androstenedione or the potent anti-glucocorticoid, RU486. Individual mice received 100 mg of the indicated steroids or the vehicle alone immediately post-burn (day 0), and further 50 mg doses every 24 hours for the duration of the experiment. The ear swelling response of each individually marked mouse was recorded at the pre-burn stage, and at 12, 24 and 48 hours post-burn.

Figure 2:
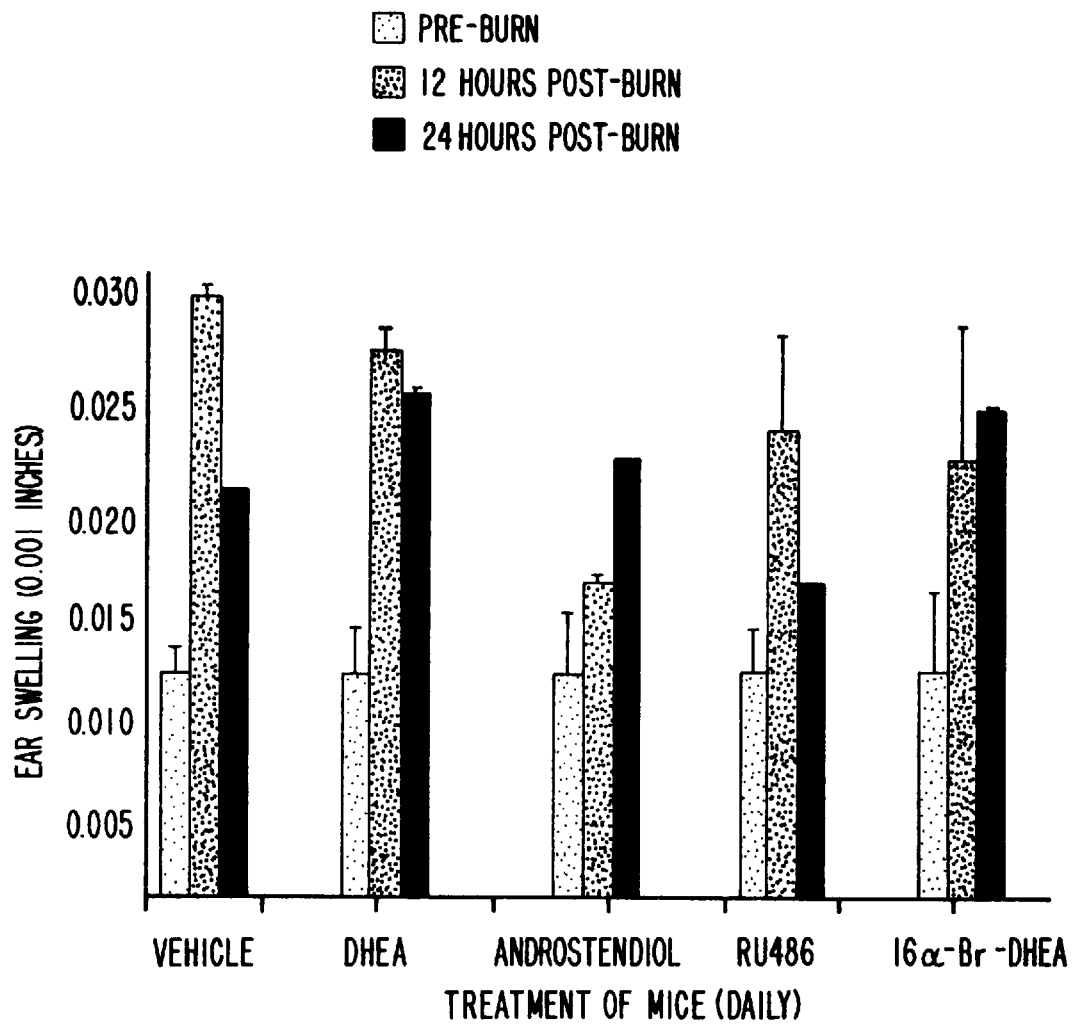
FIG. 2 shows the analysis of edema formation (ear swelling) and resolution in the burned ears of control mice and mice treated with DHEA, androstenediol, 16α-bromo-DHEA or the known anti-glucocorticoid RU486.
Figure 3A:
FIG. 3A shows the capacity of DHEA to protect against most of the progressive ischemia consequences of thermal injury to the ear.
Figure 3B:
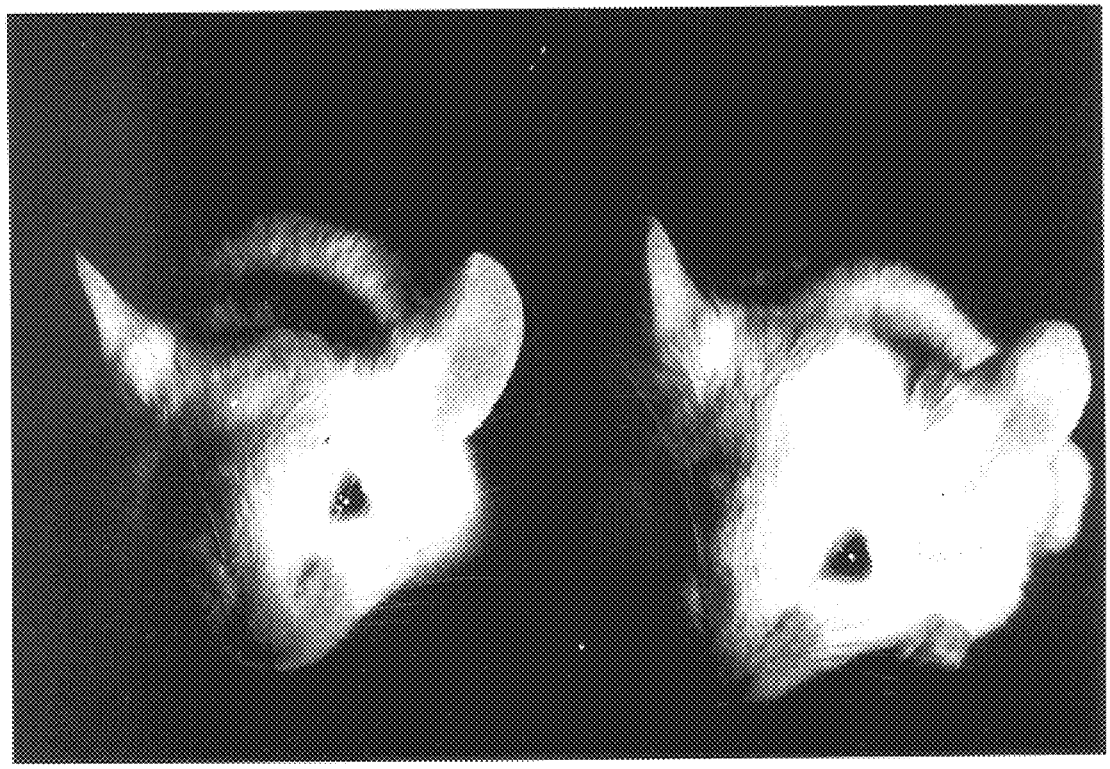
FIG. 3B shows the capacity of androstenediol to protect against most of the progressive ischemia consequences of thermal injury to the ear.
Figure 3C:
FIG. 3C shows the capacity of 16α-bromo-DHEA to protect against most of the progressive ischemia consequences of thermal injury to the ear.
Figure 3D:
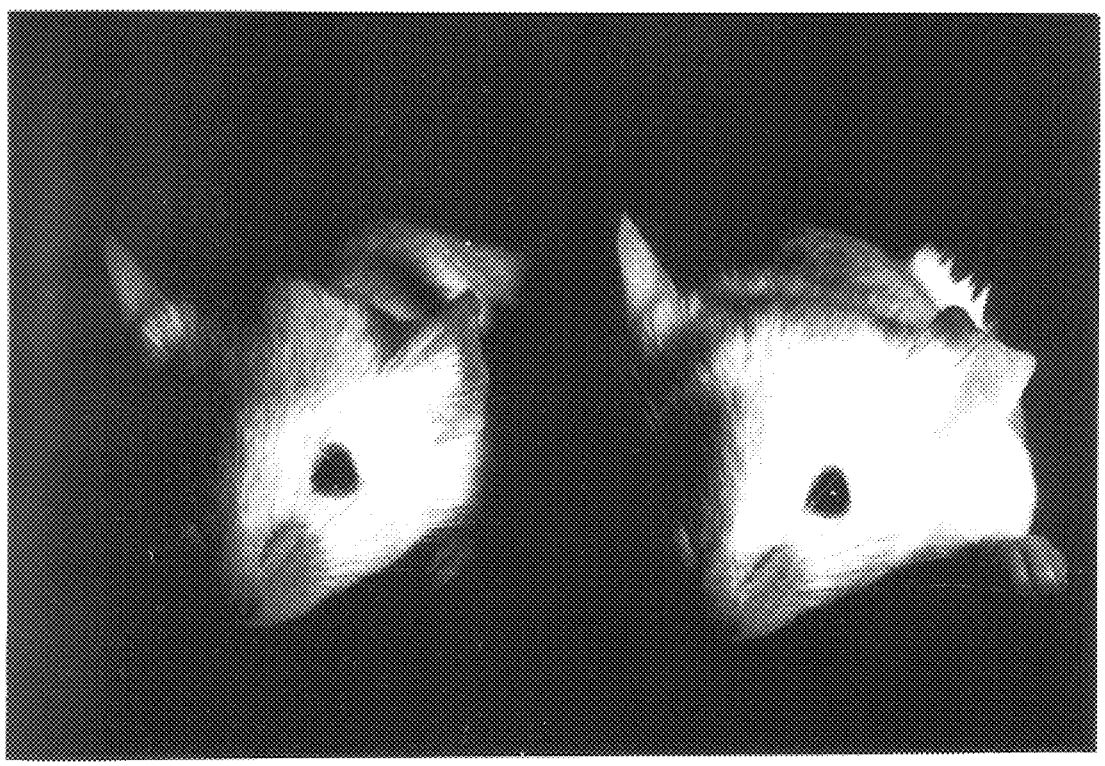
FIG. 3D shows the progressive ischemic consequences of thermal injury to the ear when vehicle alone is administered.
Figure 3E:
FIG. 3E shows the progressive ischemic consequences of thermal injury to the ear when androstenedione alone is administered.
Figure 3F:
FIG. 3F shows the progressive ischemic consequences of thermal injury to the ear when RU486 alone is administered.

Burned ears of mice being treated therapeutically with androstenediol, DHEA, or the non-metabolizable, synthetic derivative of DHEA, 16α-bromo-DHEA, each developed significant ear-swelling in response to burn injury (FIG. 2)

ear but also somehow protects the affected tissue from progressive damage by inhibiting the development of ischemia within the zone of stasis and the ultimate development of necrosis of this area. Similar results are obtained for the DHEA derivatives described above.

In similar experiments, it was found that 16α-hydroxy-DHEA was less protective, i.e., reduced the extent of, but did not totally prevent progressive ischemia, and 16α-chloro-DHEA was slightly protective against progressive ischemia.

EXAMPLE 4

Figure 4:
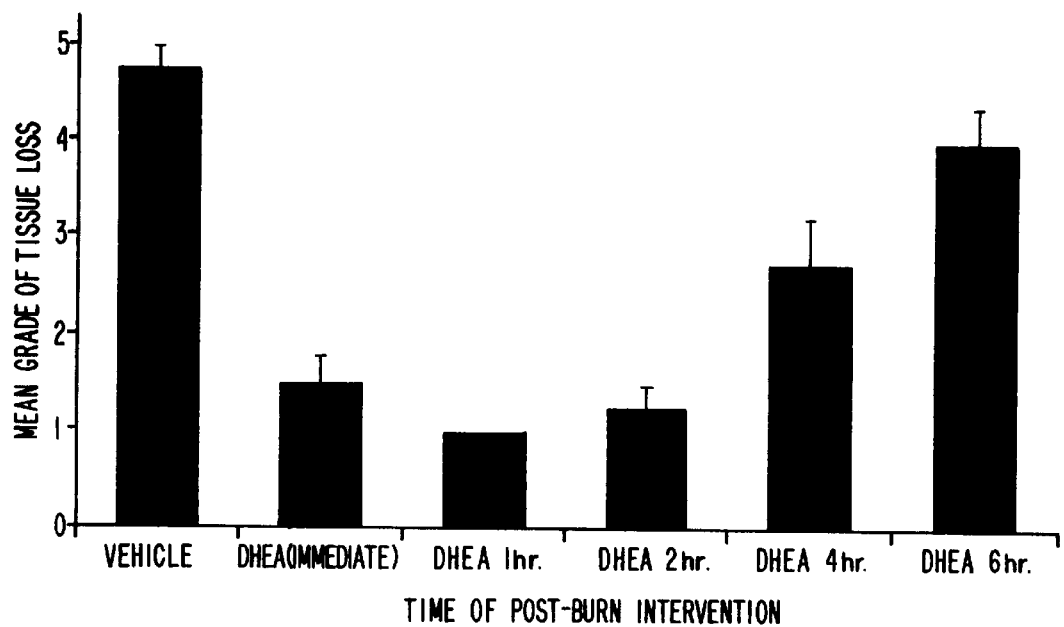
FIG. 4 shows the effect of treatment with DHEA on progressive ischemia when administered from 0–6 hours post-thermal injury.

An experiment was designed to determine whether intervention using DHEA must be delivered immediately, or whether the intervention can be delayed for up to several hours following burn injury. Mice were anesthetized, administered a burn and then, while under anesthesia, four mice were given vehicle alone, four mice were given 100 mg DHEA, and the remaining mice were divided into additional groups of four. All of the mice in a single group would receive 100 mg DHEA either one, two, four or six hours after thermal injury. Tissue loss by each mouse was evaluated 72 hours after thermal injury, and the results of the scoring are presented in FIG. 4.

This Figure demonstrates that intervention using DHEA can be delayed for up to two hours with no significant difference in the protective effects of DHEA mean grade of 1.25% 0.25 (p=<0.001). Even with a delay of four hours before administration of DHEA, a mean score of 2.75% 0.479 was observed (p=<0.016). With a six-hour delay in delivery of DHEA, the mean score in tissue loss was 4.0% 0.408 and was determined to be significantly different from the group that received DHEA immediately after thermal injury (p=<0.058). It was concluded that the events which hours after thermal injury. It has now been discovered that if a sufficiently high dose of DHEAS is administered intravenously, following the traumatic injury, such that an equivalent amount of DHEA as used in this experiment is produced in the body, then DHEAS is protective. Similar results are obtained for the DHEA derivatives described above.

The above Examples were repeated, in which 150 mg of DHEAS was administered intravenously in place of the DHEA. In these examples, the same results were obtained with DHEA as with DHEAS.

EXAMPLE 5

Effect of DHEA on Reperfusion Injury

Male Sprague-Dawley rats weighing 130–170 g were randomly assigned to no pre-treatment, vehicle pre-treatment or DHEA pre-treatment (4 mg/kg). Animals were treated with vehicle or DHEA the day before and the day of surgery. Anesthesia was induced with intraperitoneal pentobarbital (60–70 mg/kg). The rats were placed on a heating pad, and body temperature (measured by rectal probe) was maintained at between 35–37° C. Detection of the cremaster muscle on its neurovascular pedicle was performed according to conventional techniques (78–80). Briefly, a skin incision is made from the anterior iliac spine to the tip of the scrotum. The testis with cremaster muscle intact is then dissected away from the scrotum. An opening of 1 cm is made on the ventral surface of the cremaster, and the testis and spermatic cord are removed. Under a microscope, the neurovascular pedicle, consisting of the pubic-epigastric arteries, vein, and genitofemoral nerve, is then completely isolated by dissecting to the origin of the vessels from the external iliac artery and vein. Finally, the front wall of the cremaster muscle sac is opened and the island cremaster muscle flap is prepared for intravital videomicroscopy. The rat is secured on a specially designed tissue bath, and the cremaster muscle flap is spread over the coverglass in the opening at the bottom of the bath and fixed with 5-0 silk sutures. It is then transilluminated from below, using a fiberoptic tungsten lamp. The muscle is kept moist and covered with impermeable plastic film. The tissue bath, designed specifically for temperature control, is filled with 0.9% saline and the temperature maintained at between 35° C.–36° C. The microscope is equipped with a color video camera. The video image of the microcirculation is displayed on a 19" monitor, where the final magnification is ×1800. Measurement of microvascular activity is recorded after isolation of the muscle to establish the pre-ischemia baseline. After proper positioning of clamps to completely shut down blood flow to the muscle flap, the duration of the ischemic period is six hours. Following removal of clamps to induce reperfusion injury, activity in the microvasculature is measured at 30, 60 and 90 minutes post-reperfusion. In all experimental subjects, ischemia is followed by reflow and then by an initial period of flow of blood through the microcirculation. This burst of circulatory activity is followed by marked reperfusion injury that induces loss of flow.

The following parameters are used to evaluate the state of the cremaster muscle microvasculatory system prior to ischemia and after reperfusion.

Figure 5A:
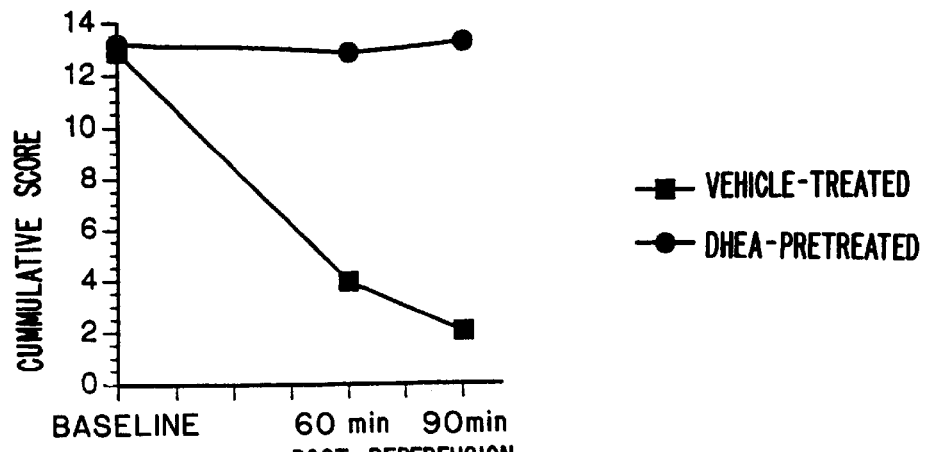
FIG. 5A shows the number of flowing capillaries in proximity to post-capillary venule in Zone 1 during reperfusion injury.
Figure 5B:
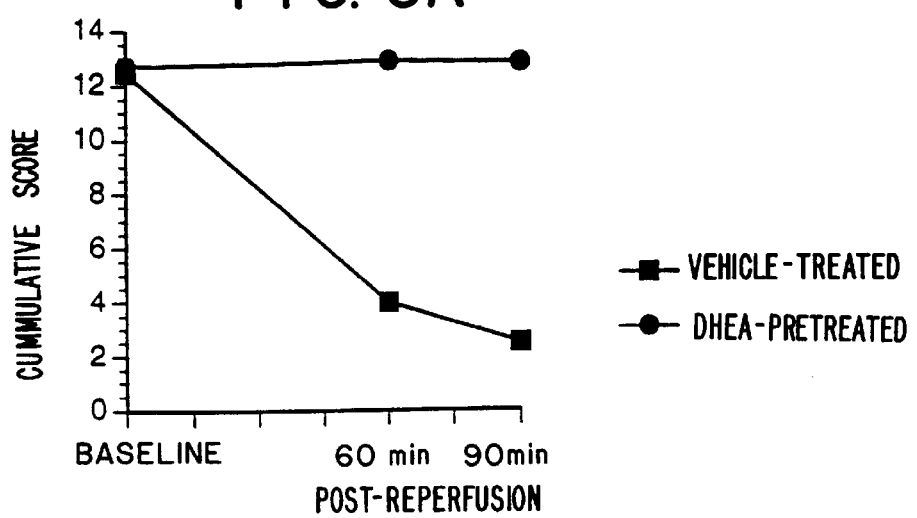
FIG. 5B shows the number of flowing capillaries in proximity to post-capillary venule in Zone 2 during reperfusion injury.
Figure 5C:
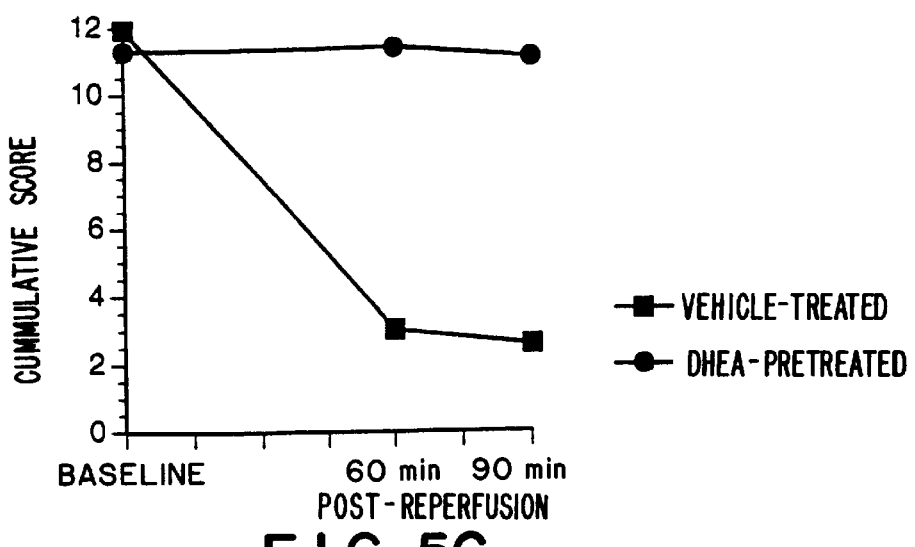
FIG. 5C shows the number of flowing capillaries in proximity to post-capillary venule in Zone 3 during reperfusion injury.

1) Density of Perfused Capillaries. The density of perfused capillaries in each of three flap regions (Zone 1, 2 and 3) is measured by counting the number of flowing capillaries in proximity to the preselected post-capillary venule. Nine visual fields of capillaries are counted at each postcapillary venule site, for a total of 27 fields per cremaster muscle flap. Results are shown in FIGS. 5A, 5B and 5C for Zones 1, 2 and 3, respectively.

Figure 6A:
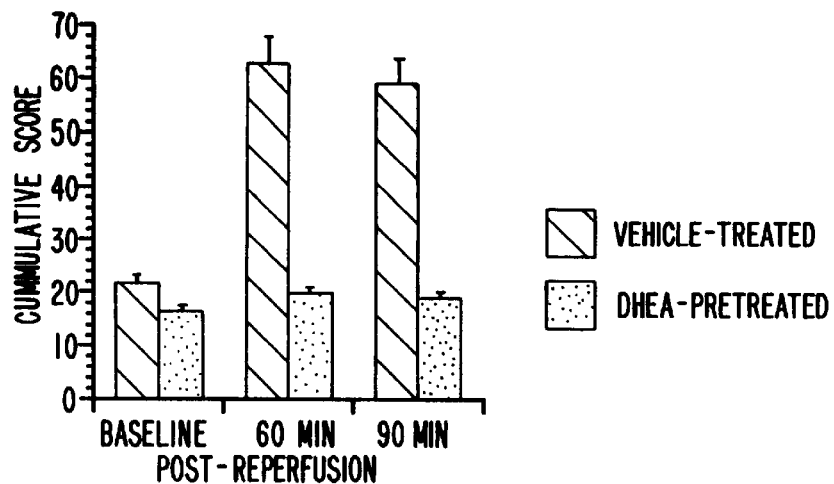
FIG. 6A shows the number of leukocytes rolling through the lumen of post-capillary venules in a two-minute period.
Figure 6B:
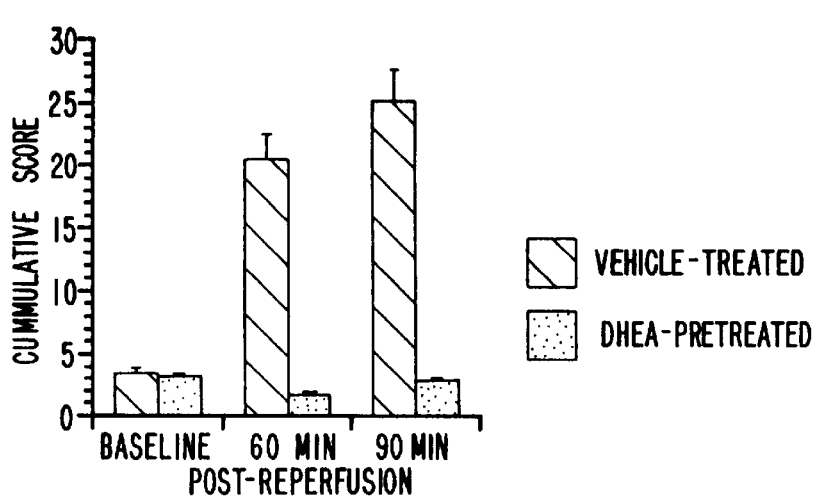
FIG. 6B shows the number of leukocytes adhering or sticking to the lumen of post-capillary venules in a two-minute period.
Figure 6C:
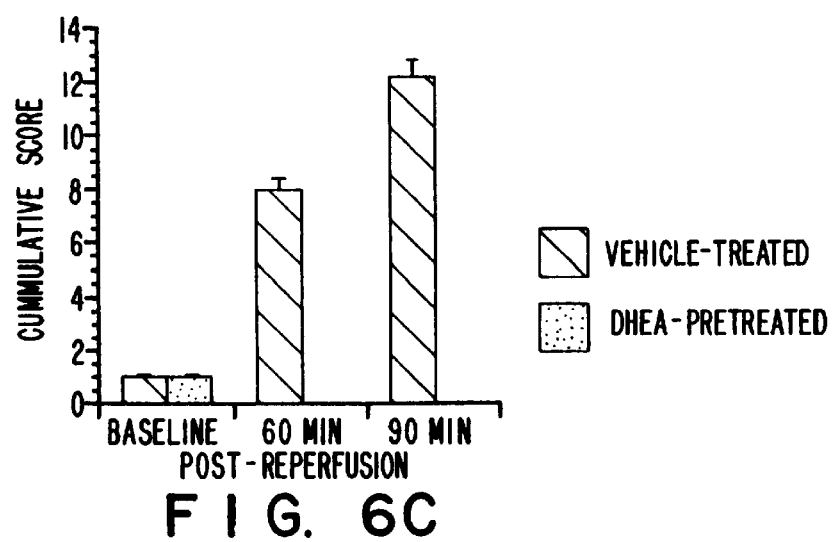
FIG. 6C shows the number of leukocytes migrating across the endothelium in a two-minute period.

2) Leukocyte Count in Postcapillary Venules. Video scans of three pre-selected post-capillary venules are taken in proximal, middle and distal flap regions. For each venule, the number of leukocytes rolling through the lumen, the number adhering to the endothelium and the number having migrated across the endothelium over a two-minute period are recorded. Results are shown in FIGS. 6A, 6B and 6C for rollers, strikers and diapedesis, respectively.

Figure 7A:
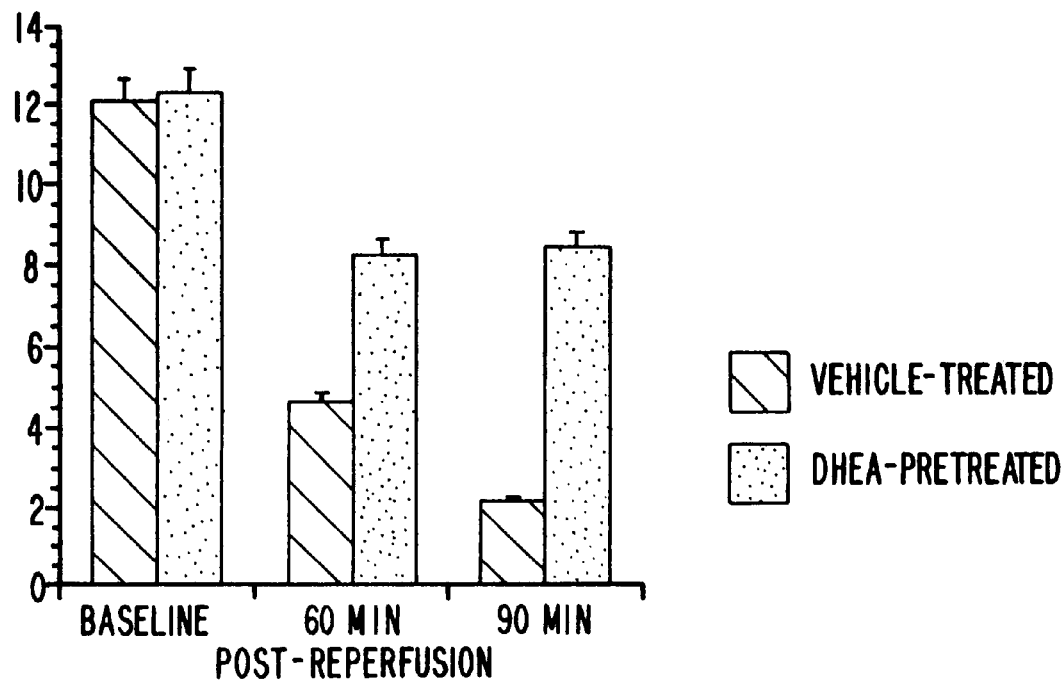
FIG. 7A shows red cell velocity of venous blood post-reperfusion.
Figure 7B:
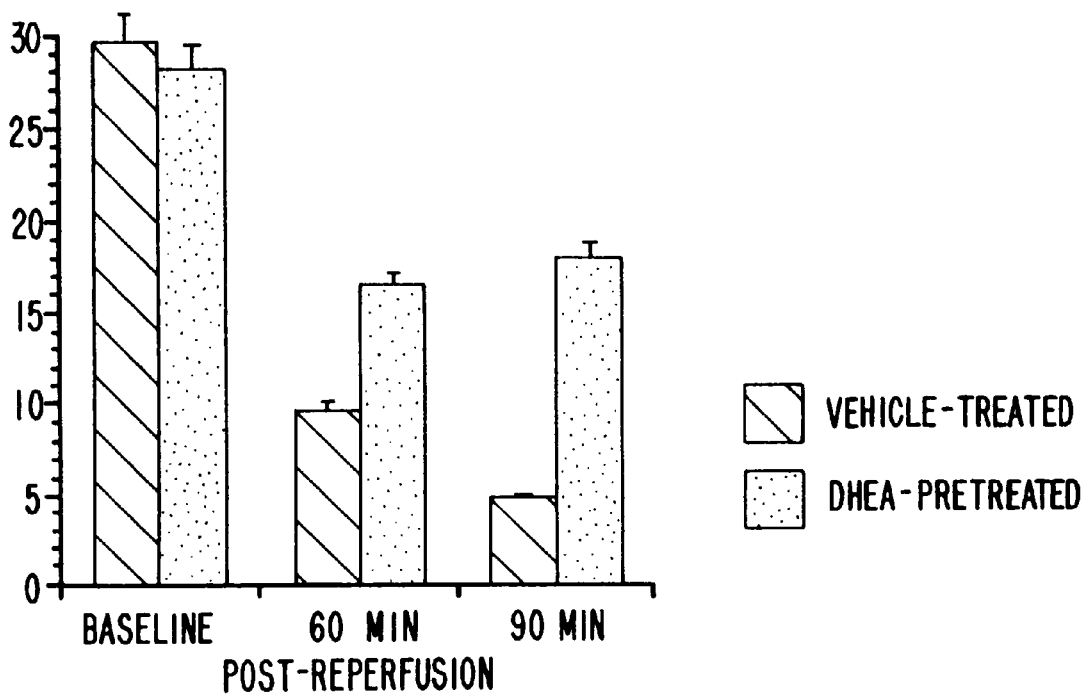
FIG. 7B shows red cell velocity of arterial blood post-reperfusion.

3) Red Blood Cell Velocities in A1 (First Order) and A2 (Second Order) Arterioles. Red blood cell velocities are recorded in the main arterioles of the cremaster flap using a custom-made optical Doppler velocimeter. Results are shown in FIGS. 7A and 7B, for velocity of venous and arterial blood, respectively.

A. Reperfusion Injury in Untreated and Vehicle-Treated Rats

Six rats were untreated and six rats were pre-treated with vehicle. Under conditions of six hours of ischemia and 90 minutes of reperfusion, the absolute number of rolling, sticking and transmigrated leukocytes increased dramatically within 60 minutes of reperfusion and showed a further increase at 90 minutes (FIGS. 6A–6C). A dramatic decrease was observed in the absolute number of perfused capillaries per high-powered field that were at both 30 and 60 minutes post-reperfusion, with a continued decrease in numbers of flowing capillaries at 90 minutes post-reperfusion (FIGS. 5A–5C). Likewise, red cell velocites in A2-sized vessels were significantly slower at 60 and 90 minutes post-reperfusion (FIGS. 7A and 7B).

B. Reperfusion Injury in DHEA-Treated Rats

Under conditions where rats were pre-treated with 4 mg/kg DHEA by subcutaneous injection the day before and the day of surgery, a marked and highly significant protective effect of the therapy was measured. All three parameters exhibited values that were close to, or identical with normal values. Of major importance, it was noted that all timepoints, endothelial-adherent properties were unchanged from baseline values. This conclusion is based on the fact that numbers of rolling, sticking and transmigrating leukocytes appeared remarkably similar to baseline values (FIGS. 6A–6C). Red cell velocities in A2 arterioles were slower to return to normal rates of flow, with velocities in some areas measuring 75% of normal at 90 minutes post-reperfusion (FIGS. 7A and 7B). At the 90-minute timepoint, the number of capillaries flowing in the microvasculature were not significantly different from the baseline values obtained prior to ischemia (FIGS. 5A–5C).

When DHEAS is substituted for DHEA at a dose 1.5 times that of the DHEA used, similar results are obtained. Similar results are obtained for the DHEA derivatives described above.

Without being bound by any theory of the physiological and biochemical operation of the DHEA congeners, it is believed that the anti-ischemic effects of these compounds are due to their activity on the adhesion of neutrophils to endothelial cells. Thus, these compounds are effective in preventing or reducing ischemia which may result from other types of tissue injury, which can be modulated by affecting adhesion to endothelial cells. This inhibition of neutrophil adhesion prevents activation of neutrophils and transmigration to the tissue side of the endothelium. Since transmigration of neutrophils is inhibited, neutrophil-induced massive damage to endothelial cells and parenchymal cells is prevented. Since neutrophil activation is prevented, production of cellular factors (by neutrophils) which leads to platelet aggregation is also prevented. Thus, progressive tissue necrosis is prevented or reduced. In addition, the progressive ischemia of gut tissue (leading to bacterial translocation) and of the epidermis and of cardiac muscle and the ischemia of the alveolar wall (leading to ARDS) are mediated through similar mechanisms. Thus, these compounds are also effective in preventing or reducing bacterial translocation and ARDS.

EXAMPLE 6

Effect of DHEA on Expression of P-Selectin by Platelets

Platelets were fractionated from freshly drawn blood (mature adults and elderly). Platelets were either utilized unwashed or washed. Washed platelets were obtained by conventional procedures (81, 82). Briefly, blood was collected to a syringe containing 1 volume of anticoagulant (0.085 M sodium citrate, 0.065 M citric acid, 2% dextrose) to 7 volumes of blood. Routinely, 50 ml of blood was withdrawn, Blood samples were centrifuged at 180 xg for 15 minutes at room temperature to sediment red and white blood cells. The upper two-thirds of the platelet-rich plasma supernatant was carefully removed by aspiration, and the platelets were pelleted by centrifugation at 1100 xg for 10 minutes at room temperature. The supernatant was decanted and the platelets were resuspended by gently mixing the sample in 2 ml of washing buffer (Tyrode's buffer without calcium, pH 6.50 at 37° C.). The platelet suspension was then diluted to a volume equal to the original volume of blood drawn with Tyrode's buffer, and centrifuged at 1100 xg for 10 minutes at room temperature. The platelets were washed twice more by centrifugation and resuspended in 5 ml of incubation buffer (washing buffer adjusted to pH 7.4 at 37° C.). The platelets were counted in a Neubauer hemocytometer.

Washed and unwashed platelets were examined for the presence of P-selectin by direct immunostaining. Platelets ($1\times10^6$) were incubated with phycoerythrin-conjugated either negative control antibody or anti-human P-selectin monoclonal antibody (CD62 antibody, CAMFolio, Becton-Dickinson) for 15 minutes on ice. After that time, samples were washed twice with staining buffer (PBS, 0.1% sodium azide, 2% fetal bovine serum), reconstituted in 500 $\mu$l of staining buffer and analyzed by a FACScan flow cytometer (Becton Dickinson). The fluorescence was displayed as a single parameter histogram on a linear scale.

Measurement of P-selectin levels on surface of washed platelets obtained from blood of mature individuals showed that approximately 50% of washed platelets (resting platelets) tested positive for the presence of P-selectin. Sixty-eight percent of the unwashed platelets obtained from blood of an elderly individual tested positive for P-selectin. When whole blood form this individual was supplemented with 10 $\mu$M final concentration of DHEA prior to fractionation of the platelets and then test, only 12% of the platelets stained positive for P-selectin. This down-regulation of P-selectin by DHEA was accompanied by a 40% reduction in thrombin activated platelet aggregation. When this latter individual was placed on a supplemental therapy with DHEAS and the platelets fractioned from blood drawn during the supplemental therapy with DHEAS, the platelets were refractory to exogenous DHEA when activated with the same amount of thrombin as activated prior to the therapy. Thus, the observed down-regulation of P-selectin on the surface of platelets from elderly individuals by DHEA was accompanied by a prevention of thrombin-stimulated aggregation of these platelets by DHEA.

When DHEAS is used in place of DHEA at 1.5 times the DHEA dose, similar results are obtained. Similar results are obtained for the DHEA derivatives described above.

EXAMPLE 7

Effect of DHEA on Expression of P-Selectin by Endothelial Cells

Non-virally transformed Human Dermal Microsvascular Endothelial cells were cultured using conventional techniques. Cells in passage number 2 were put on cover slips covered with attachment factor, and were grown in serum free system without phebol red until they became confluent. Groups of cells were incubated with vehicle alone or with 1 $\mu$M, 10 $\mu$M, 25 $\mu$M, 50 $\mu$M or 100 $\mu$M DHEA at 37° C. for 10 minutes. The cells were then activated with $10^{-5}$ M histamine or with Dulbecco's phosphate buffer saline (dPBS) at 37° C. for 5 minutes.

The cells were then examined by indirect immunostaining/fluorescence microscopy. Briefly the cells were first washed 2–3 times in dPBS containing 1% bovine serum albumin (BSA), 1–2 minutes per wash. The cells were then fixed in ice-cold methanol for 5–7 minutes and then washed 2–3 times in dPBS containing 1% BSA and 0.01% azide. The cells were then incubated with anti P-selectin antibody at 4° C. in a humified chamber for 30 minutes. The cells were then washed 2–3 times in dPBS containing 1% BSA at 4° C., 1–2 minutes per wash. The cells were then is incubated an anti anti-body linked to P-phycoerytherin at 4° C. for 30–40 minutes, after which the cells were washed 2–3 times in dPBS containing 1% BSA at 4° C., 1–2 minutes per wash. The slides are then mounted and and P-selectin expression on endothelium is examined in fluorescence microscopy using rhodamine filterset.

Similary results are noted as seen for P-selectin expression in platelets. Namely, DHEA at concentrations of 10 $\mu$M or greater prevented the up-regulation of P-selectin expression normally observed on endothelium in response to histamine. The endothelium incubated with DHEA prior to histamine activation looked similar to the control, non-activated endothelium.

When DHEAS is used in place of DHEA, similar results are obtained. Similar results are obtained for the DHEA derivatives described above.

EXAMPLE 8

Effect of DHEAS on Hemorrhagic Shock

CF-1 mice, age 6–8 months, were anesthetized using methoxyflurothane and prepared for abdominal surgery. To maintain the required surgical level of anesthesia, methoxyflurothane was used as needed in a nose cone apparatus. Each mouse was tested for the level of respiration, eye blink response and response to a skin pinch to ensure a level of anesthesia appropriate for surgery. The duration of abdominal surgery was approximately two hours, during which time 35–40% of the animal's blood volume is removed over a 30 minute period. The removal of blood in a controlled manner simulates the effect of hemorrhagic shock. A slow intravenous infusion of the removed blood and a 2X volume of resuscitation fluid (lactated Ringers solution) into a central vein was made. The resuscitation fluid was supplemented with either 2 mg DHEAS or the excipient as a placebo. The peritoneum and overlying skin were sutured separately.

Animals were maintained at 38°–39° C. until recovery is complete. Under these conditions, most of the placebo-treated animals died within 24–48 hours. Four hours after surgery, a colony forming unit (CFU) assay for bacteria was performed and malondialdehyde in liver was assayed using conventional techniques. Briefly, mesenteric lymph nodes (MLN) were removed and cultured on blood agar plates and the number of CFUs counted following culturing. The liver was removed and the amount malondialdehyde was measured. The survival rate, CFUs and malondialdehyde results are shown in Table 2.

TABLE 2

| Treatment Group | Survival at 48 Hours | CFU at 4 Hours Post Surgery ($10^6$/MLN cells) | Malondialdehyde in Liver in 4 Hours (mMol) |
|---|---|---|---|
| Sham | 15/15 | 0.8 | 0.035 |
| Vehicle-treated, shock/resuscitation | 1/15 | 12,020 | 0.226 |
| DHEAS-treated, shock/resuscitation | 13/15 | 7.14 | 0.076 |

When DHEA is used in place of DHEAS, similar results are obtained. Similar results are obtained for the DHEA derivatives described above.

EXAMPLE 9

Effect of DHEA on Hypoxia-Induced Pulmonary Vasoconstriction

Isolated perfused ferret lungs are an established animal model to study secondary pulmonary hypertension, and were used in this example. In brief, male ferrets were anesthetized i.p. with pentobarbital sodium and the chest was opened. Stainless steel cannulae were secured in the left atrium and pulmonary artery, and the pulmonary artery and the aorta were ligated. The lungs were perfused with a mixture of autologous blood and Krebs-Henseleit buffer in a circulating manner at a constant rate of 85 ml/min. The perfusion circuit included a perfusate reservoir, a roller perfusion pump, filter, and a heat exchanger. The perfusion system was made of tygon tubing used for connections and for passage through the perfusion pump. The temperture of the perfusate was kept between 37 and 38° C., the pH was maintained at 7.35 to 7.40 by adding sodium bicarbonate to the reservoir as needed. The venous reservoir was placed below the lowermost portion of the lung.

The lungs were ventilated with a hypoxic gas mixture of 5% $CO_2$, 4% $O_2$, and 91% $N_2$ via a tracheotomy with a Harvard animal respirator for 30 minutes. The animals were ventilated with a tidal volume of 30 ml, at a rate of 18 breaths/min. and with 2 cm $H_2O$ positive end-expiatory pressure. For measurements, pulmonary arterial, left atrial and tracheal pressures were monitored using Gould Statha P231D pressure transducers connected to the inflow circulation and recorded on a Grass polygraph. After 30 minutes of ventilation with hypoxic gas mixture, DHEA in a dose between 8–12 mg/kg body weight was added to reservoir, and perfusate was allowed to perfuse ferret lungs for 1.5 hours. A sudden drop to baseline level in pulmonary artery pressure was obserted upon DHEA delivery. Pulmonary artery pressure remained at basal level until the end of the experiment, i.e., a total of two hours. These results demonstrate the vasodilatory effect of DHEA in pulmonary circulation constricted in response to hypoxia. DHEA treatment lowered pulmonary pressure completely to normal, and this lowering of pressure was sustained. When compared with nitric oxide (a therapeutic agent conventionally used) in the same model, DHEA was more potent in reducing pulmonary artery pressure. The effect of nitric acid lasted for only minutes, whereas the effect of DHEA lasted for at least two hours. Similar results are obtained for the DHEA derivatives described above.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES (1) Merrill, S. W. et al. (1987). Am. J. Surg. 154:623.
(2) Faist, E. et al. In: Faist, E. (ed.) Immune Consequences of Trauma, Shock and Sepsis, Vol. 17, Springer-Verlag, Berlin, Heidelberg (p. 79).
(3) Baue, A. E. (1993). Ann. Thorac. Surg. 55:822–9.
(4) Saadia, R. et al. (1990). Br. J. Surg. 77:482–92 (1990).
(5) Willmore, D. W. et al. (1988). Surgery 104:917–23.
(6) Ertel, W. et al. (1990). J. Surg. Res. 48:622.
(7) Faist, E. et al. (1986). Arch. Surg. 121:1000.
(8) Waage, A. et al. (1989). J. Exp. Med. 169:333.
(9) Faist, E. et al. (1989). J. Trauma 29:2.
(10) Wood, J. J. et al. (1984). Ann. Surg 200:311.
(11) Takayama, T. K. et al. (1990). Arch. Surg. 125:29.
(12) Arturson, G. et al. (1969). Lancet 1:546 (1969).
(13) Daniels, J. C. et al. (1974). J. Trauma 14:137.
(14) Mosmann, T. R. et al. (1989). Ann. Rev. Immunol. 7:145.
(15) Teodorczyk-Injeyan, J. A. (1989). Clin. Immun. Immunopath. 51:205.
(16) Faist, E. et al. (1988). Arch. Surg. 123:287.
(17) Wood, J. J. et al. (1987). Arch. Surg. 122:179.
(18) O'Mahony, J. B. et al. (1984). J. Trauma 24:869.
(19) Damas, P. et al. (1989). Crit. Care Med. 17:975.
(20) Van Snick, J. (1990). Ann. Rev. Immunol. 8:253.
(21) Satch, T. et al. (1988). Mol. Cell Biol. 8:3546.
(22) Wilmore, D. W. (1974). Ann. Surg. 180:653.
(23) Wilmore, D. W. (1976). Surg. Gynecol. Obstet. 142:257.
(24) Bessey, P. Q. (1976). Ann. Surg. 200:264.
(25) Parker, L. et al. J. Clin. Endocrinol. Metab. 60:947.
(26) Araneo, B. A. et al. (1993). Arch. Surg. 128:318–325.
(27) Jonat, G. et al. (1990). Cell 622:1189.
(28) Schule, R. et al. (1990). Cell 62:1217.
(29) Yamamoto, K. R. (1985). Ann. Rev. Genet. 19:209.
(30) De Peretti, E. et al. (1978). J. Clin. Endocrinol. Metab. 47:572.
(31) Swartz, A. G. et al. (1981). Nutr. Cancer 3:46.
(32) Yen, T. T. et al. (1977). Lipids 12:409.
(33) Coleman, D. C. (1982). Diabetes 31:830 (1982).
(34) Flood, J. F. (1988). Brain Res. 447:269
(35) Daynes, R. A. et al. (1990). Eur. J. Immunol. 19:2319.
(36) Araneo, B. A. et al. (1995). J. Surg. Res. (in press).
(38) Rodgers, G. M. (1988). FASEB J 2:116–123.
(39) Hernandez, L. A. et al. (1987). Am. J. Physiol. 253 (Heart Cir. Physiol. 22):H699-H703.
(40) Lucchesi, B. R. (1990). Am. J. Cardiology 65:14I–23I.
(41) Lehr, H. A. et al. (199). J. Clin. Invest. 87:2036–2041.
(42) Entman, M. L. et al. (1991). FASEB J 5:2529–2537.
(43) Weyrich, A. S. et al. (1993). J. Clin. Invest. 91:2620–2629.
(44) Lefer, A. M. et al. (1991). FASEB J 5:2029–2034.

(45) Brown, J. M. et al. (1988). *J. Clin. Invest.* 81:1297–1301.
(46) "Cellular Injury and Adaptation," in *Pathologic Basis of Disease*, Cotran et al., eds., WB Saunders, Philadelphia, pp. 1–81 (1989).
(47) Robson, M. C. et al. (1979). *Plastic and Recons-tructive Surgery* 63:781–787.
(48) Robson, M. C. et al. (1980). *J. Trauma* 20:722–725
(49) Rockwell, W. B. and Ehrlich, H. P. (1992). *J. Burn Care Rehab* 13:403–406.
(50) Boykin, J. V. et al. (1980). *Plastic Reconstruct. Surgery* 66:191–198.
(51) Morehouse, J. L. et al. (1986). *Gastroenterol* 91:673–682.
(52) Maejimak, et al. (1984). *Arch. Surg.* 119:166–172.
(53) Czaja, A. J. et al. (1974). *N. Engl. J. Med.* 291:925–929
(54) Seavitt, S. (1967). *Br. J. Surg.* 54:32–41.
(55) Desai, M. H. et al. (1991). *Surgery, Gyn. Obstet.* 172:257–261.
(56) Deitch, E. A. and R. Berg (1987). *J. Burn Rehab.* 8:475–482.
(57) Simon, R. H. and Ward, P. A. (1992). In *Inflammation: Basic Principles and Clinical Correlates*, 2d Ed., Galin, J. I. et al., Eds., Raven Press, Ltd., New York, pp. 999–1016.
(58) (1979). *N. Eng. J. Med.* 300:213.
(59) (1973). *Med. Clin. North Am.* 57:637.
(60) (1976). *Am. Rev. Resp. Dis.* 114:775.
(61) (1980). *Ann. Intern. Med.* 93:391.
(62) (1981). *Lancet* 1:681.
(63) Madden, J. A. et al. (1985). *J. Appl. Physiol.* 59:113.
(64) Hoshino, Y. et al. (1988). 65:2468.
(65) Bergofsky, E. H. et al. (1967). 20:506.
(66) Harder, D. (1985). *J. Appl. Physiol.* 59:1389.
(67) McMurty, I. F. et al. (1976). *Circul. Res.* 38:99.
(68) Sturani, C. et al. (1983). *Chest* 84:135.
(69) Voelkel, N. F. et al. (1981). *J. Clin. Invest.* 67:238.
(70) Farrukh, I. S. et al. (1992). *Am. Rev. Resp. Dis.* 145:1389.
(71) Eich, D. M. et al. (1992). U.S. Pat. No. 5,110,810.
(72) Eich, D. M. et al. (1 992). U.S. Pat. No. 5,162,198.
(73) Nestler, J. E. et al. (1990). U.S. Pat. No. 4,920,115.
(74) Kent, S. (1982). *Geriatrics* 37:157–159.
(75) Daynes, R. A et al. (1994). WO 94/20111.
(76) Jackson (1953). *British J. Surg.* 40:588–593.
(77) Ericksson, E. et al. (1980). *Microvascular Res.* 19:374–379.
(78) Anderson, G. L. et al. (1988). *Microvascular Res.* 36:56–63.
(79) Siemionow, M. et al. (1991). *Microcirc. Endoth. Lymphatics* 7:183–197.
(80) Siemionow, M. et al. (1993). *J. Hand Surgery* 18A:963–971.
(81) Orlinska, U., (1989). PhD Dissertation: Transforming growth factor β1 and plyamines in monocrotaline-induced pulmonary hypertension. Univ. of Kentucky, School of Pharmacy, Lexington, Ky.
(82) Hawrylowicz, C. H. et al. (1989). *J. Immunol.* 143:4015–4018.

What is claimed is:

1. A method for preventing or reducing pulmonary hypertension in a patient at risk of pulmonary hypertension which comprises administering to said patient an effective amount of a dehydroepiandrosterone (DHEA) derivative having the general formulas I or II or their pharmaceutically acceptable salts

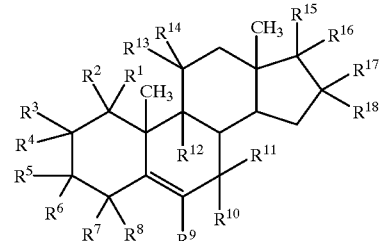

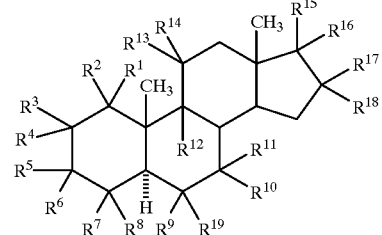

wherein
$R^1, R^2, R^3, R^4, R^6, R^7, R^8, R^9, R^{10}, R^{11}, R^{12}, R^{13}, R^{14}$ and $R^{19}$ are independently H, —OH, halogen, $C_{1-10}$ alkyl or $C_{1-10}$ alkoxy;

$R^5$ is H, —OH, halogen, $C_{1-10}$ alkyl, $C_{1-10}$ alkoxy or $OSO_2R^{20}$;

$R^{15}$ is
(1) H, halogen, $C_{1-10}$ alkyl or $C_{1-10}$ alkoxy when $R^{16}$ is —C(O)OR$^{21}$ or
(2) H, halogen, OH or $C_{1-10}$ alkyl when $R^{16}$ is H, halogen, OH or $C_{1-10}$ alkyl or
(3) H, halogen, $C_{1-10}$ alkyl, $C_{1-10}$ alkenyl, $C_{1-10}$ alkynyl, formyl, $C_{1-10}$ alkanoyl or epoxy when $R^{16}$ is OH; or $R^{15}$ and $R^{16}$ taken together are =O;

$R^{17}$ and $R^{18}$ are independently
(1) H, —OH, halogen, $C_{1-10}$ alkyl or $C_{1-10}$ alkoxy when $R^{16}$ is H, OH, $C_{1-10}$ alkyl or —C(O)OR$^{21}$ or
(2) H, $(C_{1-10}$ alkyl)$_n$amino, $(C_{1-10}$ alkyl)$_n$amino-$C_{1-10}$ alkyl, $C_{1-10}$ alkoxy, hydroxy-$C_{1-10}$ alkyl, $C_{1-10}$ alkoxy-$C_{1-10}$ alkyl, (halogen)$_m$-$C_{1-10}$ alkyl, $C_{1-10}$ alkanoyl, formyl, $C_{1-10}$ carbalkoxy or $C_{1-10}$ alkanoyloxy when $R^{15}$ and $R^{16}$ taken together are =O; or $R^{17}$ and $R^{18}$ taken together are =O or taken together with the carbon to which they are attached form a 3–6 member ring containing 0 or 1 oxygen atoms; or $R^{15}$ and $R^{17}$ taken together with the carbons to which they are attached form an epoxide ring;

$R^{20}$ is OH, pharmaceutically acceptable ester or pharmaceutically acceptable ether;

$R^{21}$ is H, (halogen)$_m$-$C_{1-10}$ alkyl or $C_{1-10}$ alkyl;

n is 0, 1 or 2; and m is 1, 2 or 3, with the provisos that
(a) $R^3$ is not H, OH or halogen when $R^1, R^2, R^4, R^6, R^7, R^9, R^{10}, R^{12}, R^{13}, R^{14}, R^{17}$ and $R^{19}$ are H and R is OH or $C_{1-10}$ alkoxy and $R^8$ is H, OH or halogen and $R^{11}$ is H or OH and $R^{18}$ is H, halogen or methyl and $R^{15}$ is H and $R^{16}$ is OH;
(b) $R^3$ is not H, OH or halogen when $R^1, R^2, R^4, R^6, R^7, R^9, R^{10}, R^{12}, R^{13}, R^{14}, R^{17}$ and $R^{19}$ are H and $R^5$ is OH or $C_{1-10}$ alkoxy and $R^8$ is H, OH or halogen and $R^{11}$ is H or OH and $R^{18}$ is H, halogen or methyl and $R^{15}$ and $R^{16}$ taken together are =O;

(c) $R^5$ is not H, halogen, $C_{1-10}$ alkoxy or $OSO_2R^{20}$ when $R_1$, $R_2$, $R_3$, $R^4$, $R^6$, $R^7$, $R^8$, $R^9$, $R^{10}$, $R^{12}$, $R^{13}$, $R^{14}$ and $R^{17}$ are H and $R^{11}$ is H, halogen, OH or $C_{1-10}$ alkoxy and $R^{18}$ is H or halogen and $R^{15}$ and $R^{16}$ taken together are =O; and (d) $R^5$ is not H, halogen, $C_{1-10}$ alkoxy or $OSO_2R^{20}$ when $R^1$, $R^2$, $R^3$, $R^4$, $R^6$, $R^7$, $R^8$, $R^9$, $R^{10}$, $R^{12}$, $R^{13}$, $R^{14}$ and $R^{17}$ are H and $R^{11}$ is H, halogen, OH or $C_{1-10}$ alkoxy and $R^{18}$ is H or halogen and $R^{15}$ is H and $R^{16}$ is H, OH or halogen.

2. The method of claim 1, wherein $R^{15}$ is H, halogen, $C_{1-10}$ alkyl or $C_{1-10}$ alkoxy and $R^{16}$ is —C(O)O$R^{21}$.

3. The method of claim 1, wherein $R^{15}$ is H, halogen, OH or $C_{1-10}$ alkyl and $R^{16}$ is H, halogen, OH or $C_{1-10}$ alkyl.

4. The method of claim 1, wherein $R^{15}$ is H, halogen, $C_{1-10}$ alkyl, $C_{1-10}$ alkenyl, $C_{1-10}$ alkynyl, formyl, $C_{1-10}$ alkanoyl or epoxy and $R^{16}$ is OH.

5. The method of claim 1, wherein $R^{15}$ and $R^{16}$ taken together are =O.

6. The method of claim 1, wherein the compound is administered intavenously.

7. The method of claim 1, wherein the compound is administered orally.

8. The method of claim 1, wherein the compound is administered in the amount of 1–1000 mg/kg.

9. The method of claim 1, wherein the compound is administered in the amount of 2–200 mg/kg.

* * * * *

UNITED STATES PATENT AND TRADEMARK OFFICE
CERTIFICATE OF CORRECTION

PATENT NO. : 6,150,348
DATED : November 21, 2000
INVENTOR(S) : Araneo et al.

It is certified that error appears in the above-identified patent and that said Letters Patent is hereby corrected as shown below:

Column 1,
Line 29, please insert the following paragraph before the section beginning with "BACKGROUND OF THE INVENTION":

-- STATEMENT REGARDING FEDERALLY SPONSORED RESEARCH OR DEVELOPMENT
  This invention was made with Government support under Grant No. GM46899, awarded by the National Institutes of Health, Bethesda, Maryland, and under Grant No. 0014-92-J-1612, awarded by the Department of the Navy. The United States Government has certain rights in the invention. --

Signed and Sealed this

Sixteenth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,150,348
DATED          : November 21, 2000
INVENTOR(S)    : Barbara A. Araneo et al.

It is certified that error appears in the above-identified patent and that said Letters Patent is hereby corrected as shown below:

Column 28,
Line 61, "R" should be -- $R^5$ --.

Column 29,
Line 4, "$R_1, R_2, R_3$" should be -- $R^1, R^2, R^3$ --.

Signed and Sealed this

Twenty-seventh Day of April, 2004

JON W. DUDAS
*Acting Director of the United States Patent and Trademark Office*